US006022891A

United States Patent [19]

Ross et al.

[11] Patent Number: 6,022,891

[45] Date of Patent: Feb. 8, 2000

[54] SUBSTITUTED CYCLOPROPYL PHENOXYMETHYL PHENYL CARBAMATES AND THEIR USE AS FUNGICIDES

[75] Inventors: Ronald Ross, Jamison; Ted Tsutomo Fujimoto, Churchville; Steven Howard Shaber, Horsham, all of Pa.

[73] Assignee: Rohm and Haas Company, Philadelphia, Pa.

[21] Appl. No.: 09/205,654

[22] Filed: Dec. 3, 1998

Related U.S. Application Data

[60] Provisional application No. 60/069,232, Dec. 11, 1997.

[51] Int. Cl.[7] .......................... A01N 47/20; C07C 261/02

[52] U.S. Cl. .............................................. 514/482; 560/29

[58] Field of Search ............................... 514/482; 560/29

[56] References Cited

U.S. PATENT DOCUMENTS

| | | | |
|---|---|---|---|
| 5,650,434 | 7/1997 | Ohnishi et al. | 514/538 |
| 5,824,705 | 10/1998 | Mueller et al. | 514/485 |

FOREIGN PATENT DOCUMENTS

| | | |
|---|---|---|
| 0619301A2 | 10/1994 | European Pat. Off. . |
| WO 93/15046 | 8/1993 | WIPO . |

*Primary Examiner*—Robert W. Ramsuer
*Assistant Examiner*—Dominic Keating
*Attorney, Agent, or Firm*—Guy T. Donatiello

[57] ABSTRACT

Compounds with fungicidal properties are presented having the formula $$R(CO)_m\underbrace{CR_1CR_2R_3CR_4}(CO)_n—C_6H_3(X)—OCH_2—C_6H_4—N(ZO)CO_2CH_3$$

wherein m and n are 0 or 1; X is hydrogen, halo, $C_1$–$C_4$) alkyl or alkoxy; Z is ($C_1$–$C_{12}$) alkyl or haloalkyl; R, $R_1$, $R_2$, $R_3$, and $R_4$ are independently hydrogen, a halogen, lower alkyl, alkenyl, alkynyl, alkoxy, cycloalkyl, aryl, arylcycloalkyl, or heterocyclyl, optionally substituted with one or more halogen atoms.

11 Claims, No Drawings

SUBSTITUTED CYCLOPROPYL PHENOXYMETHYL PHENYL CARBAMATES AND THEIR USE AS FUNGICIDES

This is a non-provisional application of prior pending provisional application Ser. No. 60/069,232, filed Dec. 11, 1997.

The present invention relates to benzyloxy substituted phenyl compounds, compositions containing these compounds and methods for controlling fungi by the use of a fungitoxic amount of these compounds.

It is known that carbamates of certain benzyloxy substituted phenyl compounds are useful as fungicides. The substitution of the phenyl ring is known in the art (see for example WO9315046). These compounds have met with mixed success in their use as fungicides. As a result, there is a constant need for new and effective fungicides. The problem of the provision of further fungicidal compounds is addressed by the present invention.

We have discovered phenyl derivatives which possess a substituted cyclopropyl moiety. These novel derivatives possess fungicidal properties.

The novel benzyloxy substituted phenyl compounds of the present invention have the Formula (I):

(I)

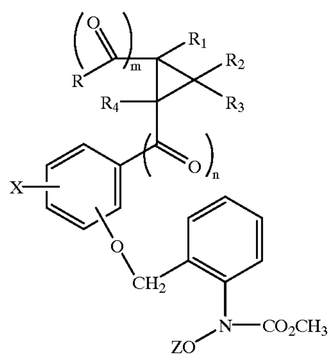

wherein m and n are the integers 0 and 1, provided that m+n is 0 or 1;

X is independently selected from hydrogen, halo, $(_1–C_4)$ alkyl, and $(C_1–C_4)$alkoxy;

Z is independently selected from $(C_1–C_{12})$alkyl and halo $(C_1–C_{12})$alkyl;

R is independently selected from hydrogen, $(C_1–C_{12})$alkyl, $(C_1–C_{12})$alkoxy, halo$(C_1–C_{12})$alkyl, halo$(C_1–C_{12})$alkoxy, $(C_2–C_{12})$alkenyl, halo$(C_2–C_{12})$alkenyl, $(C_2–C_{12})$alkynyl, halo$(C_2–C_{12})$alkynyl, $(C_1–C_{12})$alkoxy$(C_1–C_{12})$alkyl, $(C_1–C_{12})$alkoxy$(C_2–C_{12})$alkenyl, $C_1–C_{12})$alkoxy $(C_2–C_{12})$alkynyl, $(C_2–C_{12})$alkenyl$(C_1–C_{12})$alkoxy, $(C_2–C_{12})$alkynyl$(C_1–C_{12})$alkoxy, $C_2–C_{12})$alkynyl $(C_2–C_{12})$alkenyl, $(C_2–C_{12})$alkenyl$(C_2–C_{12})$alkynyl, $C_3–C_7)$cycloalkyl, halo$(C_3–C_7)$cycloalkyl, $(C_3–C_7)$ cycloalkyl$(C_1–C_{12})$alkyl, $(C_3–C_7)$cycloalkyl$(C_2–C_{12})$ alkenyl, $(C_3–C_7)$cycloalkyl$(C_2–C_{12})$alkynyl, $(C_1–C_{12})$ alkyl$(C_3–C_7)$cycloalkyl, $(C_1–C_{12})$alkoxy$(C_3–C_7)$ cycloalkyl, $(C_2–C_{12})$alkenyl$(C_3–C_7)$cycloalkyl, $(C_2–C_{12})$ alkynyl$(C_3–C_7)$cycloalkyl, halo $(C_1–C_{12})$alkyl$(C_3–C_7)$ cycloalkyl, halo$(C_1–C_{12})$alkoxy$(C_3–C_7)$cycloalkyl, halo $(C_2–C_{12})$alkenyl$(C_3–C_7)$cycloalkyl, halo$(C_2–C_{12})$alkynyl $(C_3–C_7)$cycloalkyl, halo$(C_3–C_7)$alkenyl$(C_3–C_7)$ cycloalkyl, $(C_1–C_{12})$alkoxy$(C_1–C_{12})$alkyl$(C_3–C_7)$ cycloalkyl, halo$(C_3–C_7)$cycloalkyl$(C_3–C_7)$cycloalkyl, $(C_1–C_{12})$alkoxy$(C_1–C_{12})$alkyl$(C_3–C_7)$cycloalkyl, $(C_1–C_{12})$alkoxy$(C_2–C_{12})$alkenyl$(C_3–C_7)$cycloalkyl, $(C_2–C_{12})$alkenyl$(C_1–C_{12})$alkoxy$(C_3–C_7)$cycloalkyl, $(C_1–C_{12})$alkoxy$(C_2–C_{12})$alkynyl$(C_3–C_7)$cycloalkyl, $(C_2–C_{12})$alkynyl$(C_1–C_{12})$alkoxy$(C_3–C_7)$cycloalkyl, $(C_2–C_{12})$alkenyl$(C_2–C_{12})$alkynyl$(C_3–C_7)$cycloalkyl, $(C_2–C_{12})$alkynyl$(C_2–C_{12})$alkenyl$(C_3–C_7)$cycloalkyl, $(C_3–C_7)$cycloalkyl$(C_3–C_7)$cycloalkly, $(C_1–C_{12})$alkyl $(C_3–C_7)$cycloalkyl$(C_3–C_7)$cycloalkyl, $(C_2–C_{12})$alkenyl $(C_3–C_7)$cycloalkyl$(C_3–C_7)$cycloalkyl, $(C_2–C_{12})$alkynyl $(C_3C_7)$cycloalkyl$(C_3–C_7)$cycloalkyl, $(C_1–C_{12})$alkoxy $(C_3–C_7)$cycloalkyl$(C_3–C_7)$cycloalkyl, $C_3–C_7)$cycloalkyl $(C_1–C_{12})$alkyl$(C_3–C_7)$cycloalkyl, $(C_3–C_7)$cycloalkyl $(C_2–C_{12})$alkenyl$(C_3–C_7)$cycloalkyl, $(C_3–C_7)$cycloalkyl $(C_2–C_{12})$alkynyl$(C_3–C_7)$cycloalkyl, $(C_3–C_7)$cycloalkyl $(C_1–C_{12})$alkoxy$(C_3–C_7)$cycloalkyl, $(C_3–C_7)$cycloalkyl $(C_3–C_7)$cycloalkyl$(C_3–C_7)$cycloalkyl, $(C_3–C_7)$cycloalkyl $(C_1–C_{12})$alenyl$(C_3–C_7)$cycloalkyl, $(C_3–C_7)$cycloalkyl $(C_1–C_{12})$alkoxy$(C_2–C_{12})$alkynyl$(C_3–C_7)$cycloalkyl, aryl, aralkyl, aryl$(C_1–C_{12})$alkoxy, aryl$(C_2–C_{12})$alkenyl, aryl $(C_2–C_{12})$alkynyl, aryl$(C_3–C_7)$cycloalkyl, aryloxy $(C_1–C_{12})$alkyl, aryloxy$(C_2–C_{12})$alkynyl, aryloxy $(C_2–C_{12})$alkenyl, aryl$(C_1–C_{12})$alkoxy$(C_3–C_7)$cycloalkyl, aryl$(C_2–C_{12})$alkenyl$(C_3–C_7)$cycloalkyl, aryl$(C_2–C_{12})$ alkynyl$(C_3–C_7)$cycloalkyl, aryl$(C_3–C_7)$cycloalkyl $(C_3–C_7)$cycloalkyl, $(C_3–C_7)$cycloalkylaryl, aryl$(C_1–C_4)$ alkyl$(C_3–C_7)$cycloalkyl, heterocyclic, aryl$(C_1–C_4)$ alkylheterocyclic, aryl$(C_2–C_4)$alkenylheterocyclic, aryl $(C_2–C_4)$alkynylheterocyclic, heterocyclic$(C_1–C_4)$alkyl, and heterocyclic$(C_3–C_7)$cycloalkyl;

$R_1$, $R_2$, $R_3$, and $R_4$ are independently selected from hydronge, halogan, $(C_1–C_{12})$alkyl, $(C_1–C_{12})$alkoxy, halo $(C_1–C_{12})$alkyl, $(C_2–C_{12})$alkenyl, $(C_2–C_{12})$alkynyl, $(C_3–C_7)$cycloalkyl, cyano, carboxy, $(C_{1-C4})$ alkoxycarbonyl, and aryl (additionally, $R_2$ and $R_3$ can be selected such that when taken together $R_2$ and $R_3$ form a $(C_3–C_7)$cycloalkyl ring, provided that m+0 and R and $R_1$ are not both hydrogen; and $R_5$ and $R_6$ independently selected from hydrogen, $(C_1–C_8)$ alkyl, $(C_1–C_8)$ alkoxy, halo$(C_1–C_8)$alkyl, $(C_2–C_8)$ alkenyl, $(C_2–C_8)$ alkynyl, $(C_3–C_7)$cycloalkyl, cyano, carboxy, $(C_1–C_4)$alkoxycarbonyl, and aryl.

The aforementioned $(C_1–C_{12})$alkyl, $(C_1–C_{12})$alkoxy, $(C_2–C_{12})$alkenyl, $(C_2–C_{12})$alkynyl and $(C_3–C_7)$cycloalkyl groups may be optionally substituted with up to three substituents selected from the group consisting of nitro, trihalomethyl, and cyano.

The term "alkyl" includes both branched and straight chain alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term "haloalkyl" refers to an alkyl group substituted with 1 to 3 halogens.

The term "alkoxy" includes both branched and straight chain alkyl groups from 1 to 12 carbon atoms containing at least one oxygen atom. Typical alkoxy groups are methoxy, ethoxy, n-propoxy, iso-propoxy, n-butoxy, sec-butoxy isobutoxyl, t-butoxy, n-pentoxy, isopentoxy, n-hexoxy, n-heptoxy and the like. The term "haloalkoxy" refers to an alkoxy group substituted with 1 to 3 halogens.

The term "alkenyl" refers to an ethylenically unsaturated hydrocarbon group, straight or branched, having a chain length of 2 to 12 carbon atoms and 1 to 2 ethylenic bonds. The term "haloalkenyl" refers to an alkenyl group substituted with 1 to 3 halogen atoms.

The term "alkynyl" refers to an unsaturated hydrocarbon group, straight or branched, having a chain length of 2 to 12 carbon atoms and 1 to 2 acetylenic bonds. The term "haloalkynyl" refers to an alkynyl group substituted with 1 to 3 halogens.

The term "cycloalkyl" refers to a saturated ring system having 3 to 7 carbon atoms.

The term "aryl" includes phenyl or napthyl, which maybe substituted with up to three substituents independently selected from the group consisting of halogen, cyano, nitro, phenyl, phenoxy, $(C_1–C_6)$alkyl, $(C_1–C_4)$alkylthio, $(C_1–C_4)$ alkylsulfoxide, $(C_1–C_6)$alkoxy, and halo $(C_1–C_4)$alkyl.

Typical aryl substituents include but are not limited to 4-chlorophenyl, 4-fluorophenyl, 4-bromophenyl, 2-methoxyphenyl, 2-methylphenyl, 3-methylphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term "heterocyclic" refers to a substituted or unsubstituted 5 to 6 membered unsaturated ring containing one, two, or three heteroatoms, preferably one or two heteroatoms independently selected from oxygen, nitrogen, and sulfur or to a bicyclic unsaturated ring system containing up to 10 atoms including one heteratom selected from oxygen, nitrogen, and sulfur. Examples of heterocycles include but are not limited to 2-, 3-, or 4-pyridinyl, pyrazinyl, 2-, 4-, or 5-pyrimidinyl, pyridazinyl, triazolyl, imidazolyl, 2- or 3-sthienyl, 2- or 3-furyl, pyrrolyl, oxazolyl, isoxazolyl, thiazolyl, isothiazolyl, oxadiazolyl, thiadiazolyl, quinolyl, and isoquinolyl. The heterocyclic ring may be optionally substituted with up to two substituents independently selected from $C_1–C_2$) alkyl, halogen, cyano, nitro, and trihalomethyl.

The term "aralkyl" is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl and 4-methylbenzyl. Typical phenethyl moieties are 2-(chlorophenyl)ethyl, 2-(3-chlorophenyl) ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-phenyl)ethyl, 2-(4-methylphenyl) ethyl, 2-(4-trifluoromethylphenyl)ethyl, 2-(2-methoxy phenyl)ethyl, 2-(3-methoxyphenyl)ethyl, 2-(4-methoxyphenyl)ethyl, 2-(2,4-dichlorophenyl)ethyl, 2-(3,5-dimethoxyphenyl)ethyl. Typical phenpropyl moieties are 3-phenylpropyl, 3-(2-chloro- phenyl)propyl, 3-(3-chlorophenyl)propyl, 3-(4-chlorophenyl)propyl, 3-(2,4-dichlorophenyl)-propyl, 3-(2-fluorophenyl)propyl, 3-(3-fluorophenyl)propyl, 3-(4-fluoro-phenyl)propyl, 3-(2-methylphenyl)propyl, 3-(3-methylphenyl)propyl, 3-(4-methylphenyl)ethyl, 3-(2-methoxy-phenyl)propyl, 3-(3-methoxyphenyl)propyl, 3-(4-methoxyphenyl)propyl, 3-(4-trifluoromethyl-phenyl)propyl, 3-(2,4-dichlorophenyl) propyl and 3-(3,5-dimethoxyphenyl)propyl.

Typical phenbutyl moieties include are 4-phenylbutyl, 4-(2-chlorophenyl)butyl, 4-(3-chloro-phenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3-methoxyphenyl)butyl and 4-(4-methoxyphenyl)butyl.

Halogen or halo is meant to include iodo, fluoro, bromo, and chloro moieties.

The present invention also includes salts and complexes of Formula (I), the preparation of which would be obvious to one skilled in the art. The cyclopropanes of Formula I may be obtained in preparation as stereoisometic mixtures which can be separated into individual components by conventional means. Furthermore, one skilled in the art will recognize that the addition of certain substituents to the cyclopropanes of Formula I will yield cis and trans isomers, which may also be separated by conventional menas. Substituents can be added to the compound shown in Formula (I) which would, either alone or in combination with the remainder of Formula (I), include one or more asymmetric carbon atoms. Both the individual isomeric compounds (cis and trans, stereoisomers, and other optical isomers) and mixtures thereof form subjects of the invention and can be used as fungicides.

As used throughout this invention the structures are defined to include the cis/trans and E/Z isomeric mixtures as well as optical isomers.

A preferred embodiment of this invention are the compounds, enantiomorphs and salts of Formula (I) where X is hydrogen and R is $(C_1–C_{12})$alkyl, $(C_2–C_{12})$alkenyl, $(C_2–C_{12})$alkynyl, $(C_3–C_7)$cycloalkykl, $(C_3–C_7)$cycloalkyl $(C_1–C_{12})$alkyl, $(C_3–C_7)$cycloalkyl$(C_2–C_{12})$alkenyl, $(C_1–C_{12})$alkyl$(C_3–C_7)$cycloalkyl, $(C_2–C_{12})$alkenyl$(C_3–C_7)$ cycloalkyl, $(C_3–C_7)$cycloalkyl$(C_3–C_7)$cycloalkyl, or phenyl substituted with preferably one or two substituents independently selected from halo, trihalomethyl, cyano, $(C_1–C_4)$ alkyl, $(C_1–C_4)$alkylthio, $(C_1–C_4)$alkoxy and phenyl, where the $OCH_2(2\text{-}N(OZ)CO_2CH_3\text{-aryl})$ is bonded at the meta position to the $(CO)_n$ cyclopropyl substituent of the phenyl ring as shown in Formula I'.

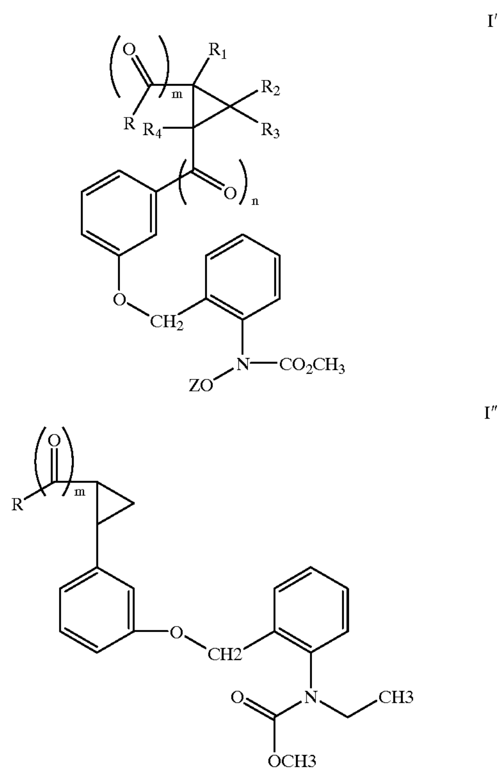

Specifically preferred are compounds where R is selected from $(C_1–C_{12})$alkyl, halo$(C_1–C_{12})$alkyl, heterocyclic, halosubstituted phenyl, $(C_1-C_4)$alkyl substituted phenyl, trihalosubstituted phenyl, $(C_3-C_7)$cycloalkyl, halo $(C_3-C_7)$ cycloalkyl, $(C_3-C_7)$cycloalkyl$(C_1-C_{12})$alkyl, $(C_3-C_7)$ cycloalkyl-$(C_2-C_{12})$alkenyl, $(C_1-C_{12})$alkyl$(C_3-C_7)$ cycloalkyl and $(C_2-C_{12})$alkenyl$(C_3-C_7)$cycloalkyl. More preferred is where R is selected from $(C_5-C_{12})$alkyl, 2-halophenyl, 3-halophenyl, 4-halophenyl, 2-$(C_1-C_4)$ alkylphenyl, 3-$(C_1-C_4)$alkylphenyl, 4-$(C_1-C_4)$alkylphenyl, cyclopropyl, cyclopropyl$(C_1-C_4)$alkyl, cyclopropyl$(C_2-C_4)$ alkenyl, $(C_1-C_4)$alkylcyclopropyl, $(C_2-C_4)$ alkenylcyclopropyl, 1-cyclopropylcyclopropyl and 2-cyclopropylcyclopropyl.

A still more preferred embodiment of this invention are the compounds, enantiomorphs, salts and complexes of Formula (I') where n is zero, m is zero or 1, R is $(C_3-C_7)$ cycloalkyl or phenyl substituted with preferably one or two substituents independently selected from halo or trihalomethyl, and $R_1$, $R_2$, $R_3$, and $R_4$ are hydrogen as shown in Formula I". Most preferred is where R is selected from 4-chlorophenyl, 4-fluorophenyl, 4-methylphenyl, 2-thienyl, 2-furyl, cyclopropyl and 1-cyclopropyl-1-propenyl.

Typical compounds encompassed by the present invention of Formula I include those compounds presented in Table 1 of Formulas II, III and IV where X=H, $R_1=R_2=R_3=R_4$=H, and n and m are zero.

TABLE 1

| Cmpd # | R |
|---|---|
| 1.01 | Ph- |
| 1.02* | Ph- |
| 1.03* | Ph- |
| 1.04 | 4-Cl(Ph)- |
| 1.05* | 4-Cl(Ph)- |
| 1.06* | 4-Cl(Ph)- |
| 1.07 | 2-Cl(Ph)- |
| 1.08* | 3-Cl(Ph)- |
| 1.09 | 2-F(Ph)- |
| 1.10 | 4-F(Ph)- |
| 1.11 | 2-$CH_3$(Ph)- |
| 1.12 | 3-$CH_3$(Ph)- |
| 1.13 | 4-$CH_3$(Ph)- |
| 1.14 | 4-$CH_3O$(Ph)- |
| 1.15 | 2-$CH_3O$(Ph)- |
| 1.16 | 2,5-Cl(Ph)- |
| 1.17 | 3,4-Cl(Ph)- |
| 1.18 | $\underline{C}H_3$ |
| 1.19 | $CH_3\underline{C}H_2$ |
| 1.20 | $CH_3CH_2\underline{C}H_2$ |
| 1.21 | $(CH_3)_2\underline{C}H$ |
| 1.22 | $CH_3(CH_2)_2\underline{C}H_2$ |
| 1.23 | $CH_3(CH_2)_4\underline{C}H_2$ |
| 1.24 | $(CH_3)_2CH\underline{C}H_2$ |
| 1.25 | $CH_3CH_2(CH_3)\underline{C}H$ |
| 1.26 | $(CH_3)_3\underline{C}$ |
| 1.27 | $(CH_3)_2CHCH_2\underline{C}H_2$ |
| 1.28 | $CH_3CH_2CH_2(CH_3)\underline{C}H$ |
| 1.29 | $CH_3CH_2(CH_3)_2\underline{C}$ |
| 1.30 | $\underline{C}F_3$ |
| 1.31 | $CF_3\underline{C}F_2$ |
| 1.32 | $CF_3\underline{C}H_2$ |
| 1.33 | $CH_2{=}\underline{C}H$ |
| 1.34 | cyclopropyl- |
| 1.35 | cyclopentyl- |
| 1.36 | cyclohexyl- |
| 1.37 | $CH_2{=}\underline{C}$(cyclopropyl) |
| 1.38 | $CH_3{-}CH{=}\underline{C}$(cyclopropyl) |
| 1.39 | $CH_3O{-}CH{=}\underline{C}$(cyclopropyl) |
| 1.40 | $C_2H_5{-}CH{=}\underline{C}$(cyclopropyl) |
| 1.41 | $CH_2{=}\underline{C}(CH(CH_3)_2)$ |
| 1.42 | $CH_3CH{=}\underline{C}(CH(CH_3)_2)$ |
| 1.43 | pyridin-3-yl |
| 1.44 | pyrimidin-2-yl |
| 1.45 | thien-2-yl |
| 1.46 | thien-3-yl |
| 1.47 | 2-naphthyl- |
| 1.48 | 2-furyl- |
| 1.49 | 3-furyl- |
| 1.50 | 2-methylcyclopropyl- |
| 1.51 | 2-ethylcyclopropyl- |
| 1.52 | 2-(n-propyl)cyclopropyl- |
| 1.53 | 2-(n-butyl)cyclopropyl- |
| 1.54 | 2-(iso-butyl)cyclopropyl- |
| 1.55 | 2-(sec-butyl)cyclopropyl- |
| 1.56 | 2-(n-pentyl)cyclopropyl- |
| 1.57 | 2-(iso-pentyl)cyclopropyl- |
| 1.58 | 2-(n-hexyl)cyclopropyl- |
| 1.59 | 2-methoxycyclopropyl- |
| 1.60 | 2-($CH_3O$)cyclopropyl- |
| 1.61 | 2-($CH_3CH_2O$)cyclopropyl- |
| 1.62 | 1-methylcyclopropyl- |
| 1.63 | 2-($CH_2{=}CH$)cyclopropyl- |
| 1.64 | 2-(1-cyclopropyl)cyclopropyl- |
| 1.65 | 2-(2-cyclopropyl)cyclopropyl- |
| 1.66 | cyclopropyl-$\underline{C}H_2$ |
| 1.67 | cyclopropyl-$CH{=}\underline{C}H$ |
| 1.68 | 2-((2'-$CH_3$)cyclopropyl) cyclopropyl- |
| 1.69 | 2-(2'-$CH_2{=}CH$) cyclopropylcyclopropyl- |
| 1.70 | 1-(Ph)cyclopropyl- |
| 1.71 | 2-(Ph)cyclopropyl- |
| 1.72 | 1-(2'-ClPh)cyclopropyl- |
| 1.73 | 2-(2'-ClPh)cyclopropyl- |
| 1.74 | 1-(3'-ClPh)cyclopropyl- |
| 1.75 | 2-(3'-ClPh)cyclopropyl- |
| 1.76 | 1-(4'-ClPh)cyclopropyl- |
| 1.77 | 2-(4'-ClPh)cyclopropyl- |
| 1.78 | 1-(2'-FPh)cyclopropyl- |
| 1.79 | 2-(2'-FPh)cyclopropyl- |
| 1.80 | 2-(3'-FPh)cyclopropyl- |
| 1.81 | 2-(4'-FPh)cyclopropyl- |
| 1.82 | 2-(2'-BrPh)cyclopropyl- |
| 1.83 | 2-(3'-BrPh)cyclopropyl- |
| 1.84 | 2-(4'-BrPh)cyclopropyl- |
| 1.85 | 2-(2'-FPh)cyclopropyl- |
| 1.86 | 2-(2'-$CH_3$Ph)cyclopropyl- |
| 1.87 | 2-(3'-$CH_3$Ph)cyclopropyl- |
| 1.88 | 2-(4'-$CH_3$Ph)cyclopropyl- |
| 1.89 | 2-(2'-$CF_3$Ph)cyclopropyl- |
| 1.90 | 2-(3'-$CF_3$Ph)cyclopropyl- |
| 1.91 | 2-(4'-$CF_3$Ph)cyclopropyl- |
| 1.92 | 1-Phcyclopentyl- |
| 1.93 | 1-Phcyclohexyl- |
| 1.94 | 2-Phcyclopentyl- |
| 1.95 | 2-Phcyclohexyl- |
| 1.96 | 2(2'-Phycyclopropyl) cyclopropyl- |
| 1.97 | 2(1'-Phycyclopropyl) cyclopropyl- |
| 1.98 | $Ph\underline{C}H_2$ |
| 1.99 | $2\text{-}ClPh\underline{C}H_2$ |
| 1.100 | $3\text{-}ClPh\underline{C}H_2$ |
| 1.101 | $4\text{-}ClPh\underline{C}H_2$ |
| 1.102 | $2\text{-}CH_3Ph\underline{C}H_2$ |
| 1.103 | $3\text{-}CH_3Ph\underline{C}H_2$ |
| 1.104 | $4\text{-}CH_3Ph\underline{C}H_2$ |
| 1.105 | 2-($PhCH_2$)cyclopropyl- |
| 1.106 | 2-(2'-$ClPhCH_2$)cyclopropyl- |
| 1.107 | 2-(4'-$ClPhCH_2$)cyclopropyl- |
| 1.108 | 2-(2'-$PhCH_2$-cyclopropyl) cyclopropyl- |
| 1.109 | 2-(1'-$PhCH_2$-cyclopropyl) cyclopropyl- |
| 1.110 | 2-(2-pyridyl)cyclopropyl- |

*Compounds 1.02, 1.05 and 1.08 refer to Formula III, compounds 1.03 and 1.06 refer to Formula IV, and the remainder of the compounds refer to Formula II. Points of attachment of each substituent to the remainder of the molecule (where not obvious) are indicated by underlining.

TABLE 1-continued

| Cmpd # | R |
| --- | --- |

II

III

IV

Typical compounds encompassed by the present invention of Formula I include those compounds presented in Table II of Formula V, VI, and VII where X=H, $R_1$=$R_2$=$R_3$=$R_4$=H, and n=0 and m=1.

TABLE II

| Cmpd # | R |
| --- | --- |
| 2.01 | Ph- |
| 2.02* | Ph- |
| 2.03* | Ph- |
| 2.04 | 4-Cl(Ph)- |
| 2.05* | 4-Cl(Ph)- |
| 2.06* | 4-Cl(Ph)- |
| 2.07 | 2-Cl(Ph)- |
| 2.08* | 3-Cl(Ph)- |
| 2.09 | 2-F(Ph)- |
| 2.10 | 4-F(Ph)- |
| 2.11 | 2-$CH_3$(Ph)- |
| 2.12 | 3-$CH_3$(Ph)- |
| 2.13 | 4-$CH_3$(Ph)- |
| 2.14 | 4-$CH_3O$(Ph)- |
| 2.15 | 2-$CH_3O$(Ph)- |
| 2.16 | 3-$CH_3O$(Ph)- |
| 2.17 | 2,4-Cl(Ph)- |
| 2.18 | $\underline{C}H_3$ |
| 2.19 | $CH_3\underline{C}H_2$ |
| 2.20 | $CH_3CH_2\underline{C}H_2$ |
| 2.21 | $(CH_3)_2\underline{C}H$ |
| 2.22 | $CH_3(CH_2)_2\underline{C}H_2$ |
| 2.23 | $CH_3(CH_2)_4\underline{C}H_2$ |
| 2.24 | $(CH_3)_2CH\underline{C}H_2$ |
| 2.25 | $CH_3CH_2(CH_3)\underline{C}H$ |
| 2.26 | $(CH_3)_3\underline{C}$ |
| 2.27 | $(CH_3)_2CHCH_2\underline{C}H_2$ |
| 2.28 | $CH_3CH_2(CH_3)\underline{C}H$ |
| 2.29 | $CH_3CH_2(CH_3)_2\underline{C}$ |
| 2.30 | $CH_2{=}CHCH_2\underline{C}H_2$ |
| 2.31 | $CH_2{=}C(CH_3)CH_2\underline{C}H_2$ |
| 2.32 | $CF_3\underline{C}H_2$ |
| 2.33 | $CH_2{=}\underline{C}H$ |
| 2.34 | cyclopropyl- |
| 2.35 | cyclopentyl- |
| 2.36 | cyclohexyl- |
| 2.37 | $CH_3O\underline{C}H_2$ |
| 2.38 | $CH_3S—CH(CH_3)$ |
| 2.39 | $PhCOCH_2\underline{C}H_2$ |
| 2.40 | $PhCH_2O\underline{C}H_2$ |
| 2.41 | pyridin-2-yl- |
| 2.42 | pyridin-3-yl- |
| 2.43 | pyrimidin-2-yl |
| 2.44 | pyrimidin-4-yl |
| 2.45 | thien-2-yl |
| 2.46 | thien-3-yl |
| 2.47 | 2-naphthyl- |
| 2.48 | 2-furyl- |
| 2.49 | 3-furyl- |
| 2.50 | 2-methylcyclopropyl- |
| 2.51 | 2-ethylcyclopropyl- |
| 2.52 | 2-(n-propyl)cyclopropyl- |
| 2.53 | 2-(n-butyl)cyclopropyl- |
| 2.54 | 2-(iso-butyl)cyclopropyl- |
| 2.55 | 2-(sec-butyl)cyclopropyl- |
| 2.56 | 2-(n-pentyl)cyclopropyl- |
| 2.57 | 2-(iso-pentyl)cyclopropyl- |
| 2.58 | 2-(n-hexyl)cyclopropyl- |
| 2.59 | 2-methoxycyclopropyl- |
| 2.60 | 2-($CH_3O$)cyclopropyl- |
| 2.61 | 2-($CH_3CH_2O$)cyclopropyl- |
| 2.62 | 1-methylcyclopropyl- |
| 2.63 | 2-($CH_2{=}CH$)cyclopropyl- |
| 2.64 | 1-(cyclopropyl)cyclopropyl |
| 2.65 | 2-(cyclopropyl)cyclopropyl |
| 2.66 | cyclopropyl-$\underline{C}H_2$— |
| 2.67 | cyclopropyl-CH=$\underline{C}$H— |
| 2.68 | 2-((2'-$CH_3$)cyclopropyl) cyclopropyl- |
| 2.69 | 2-(2'-$CH_2{=}CH$) cyclopropylcyclopropyl- |
| 2.70 | 1-Phcyclopropyl- |
| 2.71 | 2-Phcyclopropyl- |
| 2.72 | 1-(2'-ClPh)cyclopropyl- |
| 2.73 | 2-(2'-ClPh)cyclopropyl- |
| 2.74 | 1-(3'-ClPh)cyclopropyl- |
| 2.75 | 2-(3'-ClPh)cyclopropyl- |
| 2.76 | 1-(4'-ClPh)cyclopropyl- |
| 2.77 | 2-(4'-ClPh)cyclopropyl- |
| 2.78 | 1-(2'-FPh)cyclopropyl- |
| 2.79 | 2-(2'-FPh)cyclopropyl- |
| 2.80 | 2-(3'-FPh)cyclopropyl- |
| 2.81 | 2-(4'-FPh)cyclopropyl- |
| 2.82 | 2-(2'-BrPh)cyclopropyl- |
| 2.83 | 2-(3'-BrPh)cyclopropyl- |
| 2.84 | 2-(4'-BrPh)cyclopropyl- |

TABLE II-continued

| Cmpd # | R |
|---|---|
| 2.85 | 2-(2'-FPh)cyclopropyl- |
| 2.86 | 2-(2'-$CH_3$Ph)cyclopropyl- |
| 2.87 | 2-(3'-$CH_3$Ph)cyclopropyl- |
| 2.88 | 2-(4'-$CH_3$Ph)cyclopropyl- |
| 2.89 | 2-(2'-$CF_3$Ph)cyclopropyl- |
| 2.90 | 2-(3'-$CF_3$Ph)cyclopropyl- |
| 2.91 | 2-(4'-$CF_3$Ph)cyclopropyl- |
| 2.92 | 1-Phcyclopentyl- |
| 2.93 | 2-Phcyclohexyl- |
| 2.94 | 2-Phcyclopentyl- |
| 2.95 | 2-Phcyclohexyl- |
| 2.96 | 2(2-Phycyclopropyl)cyclopropyl- |
| 2.97 | 2(1-Phycyclopropyl)cyclopropyl- |
| 2.98 | $Ph\underline{C}H_2$ |
| 2.99 | $2\text{-}ClPh\underline{C}H_2$ |
| 2.100 | $3\text{-}ClPh\underline{C}H_2$ |
| 2.101 | $4\text{-}ClPh\underline{C}H_2$ |
| 2.102 | $2\text{-}CH_3Ph\underline{C}H_2$ |
| 2.103 | $3\text{-}CH_3Ph\underline{C}H_2$ |
| 2.104 | $4\text{-}CH_3Ph\underline{C}H_2$ |
| 2.105 | 2-($PhCH_2$)cyclopropyl- |
| 2.106 | 2-(2'-$ClPhCH_2$)cyclopropyl- |
| 2.107 | 2-(4'-$ClPhCH_2$)cyclopropyl- |
| 2.108 | 2-(2-$PhCH_2$cyclopropyl) cyclopropyl- |
| 2.109 | 2-(1-$PhCH_2$cyclopropyl) cyclopropyl- |
| 2.110 | 2-(2-pyridyl)cyclopropyl- |

*Compounds 2.02, 2.05 and 2.08 refer to Formula VI, compounds 2.03 and 2.06 refer to Formula VII, and the remainder of the compounds refer to Formula V. Points of attachment of each substituent to the remainder of the molecule (where not obvious) are indicated by underlining.

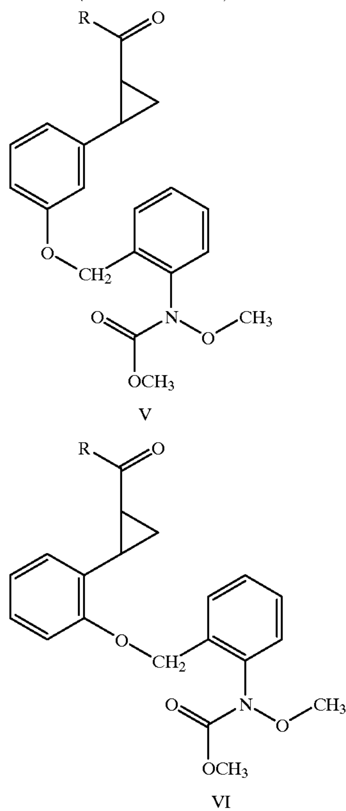

TABLE II-continued

| Cmpd # | R |
|---|---|

VII

Typical compounds encompassed by the present invention of Formula I include those compounds presented in Table III of Formula VIII, IX and X where X=H, $R_1=R_2=R_3=R_4=H$, and n=1 and m=0.

TABLE III

| Cmpd # | R |
|---|---|
| 3.01 | Ph- |
| 3.02* | Ph- |
| 3.03* | Ph- |
| 3.04 | 4-Cl(Ph)- |
| 3.05* | 4-Cl(Ph)- |
| 3.06* | 4-Cl(Ph)- |
| 3.07 | 2-Cl(Ph)- |
| 3.08* | 3-Cl(Ph)- |
| 3.09 | 2-F(Ph)- |
| 3.10 | 4-F(Ph)- |
| 3.11 | 2-$CH_3$(Ph)- |
| 3.12 | 3-$CH_3$(Ph)- |
| 3.13 | 4-$CH_3$(Ph)- |
| 3.14 | 4-$CH_3O$(Ph)- |
| 3.15 | 2-$CH_3O$(Ph)- |
| 3.16 | 2,5-Cl(Ph)- |
| 3.17 | 3,4-Cl(Ph)- |
| 3.18 | $\underline{C}H_3$ |
| 3.19 | $CH_3\underline{C}H_2$ |
| 3.20 | $CH_3CH_2\underline{C}H_2$ |
| 3.21 | $(CH_3)_2\underline{C}H$ |
| 3.22 | $CH_3(CH_2)_2\underline{C}H_2$ |
| 3.23 | $CH_3(CH_2)_4\underline{C}H_2$ |
| 3.24 | $(CH_3)_2CH\underline{C}H_2$ |
| 3.25 | $CH_3CH_2(CH_3)\underline{C}H$ |
| 3.26 | $(CH_3)_3\underline{C}$ |
| 3.27 | $(CH_3)_2CHCH_2\underline{C}H_2$ |
| 3.28 | $CH_3CH_2CH_2(CH_3)\underline{C}H$ |
| 3.29 | $CH_3CH_2(CH_3)_2\underline{C}$ |
| 3.30 | $\underline{C}F_3$ |
| 3.31 | $CF_3\underline{C}F_2$ |
| 3.32 | $CF_3\underline{C}H_2$ |
| 3.33 | $CH_2{=}\underline{C}H$ |
| 3.34 | cyclopropyl- |
| 3.35 | cyclopentyl- |
| 3.36 | cyclohexyl- |
| 3.37 | $CH_2{=}\underline{C}$(cyclopropyl) |
| 3.38 | $CH_3{-}CH{=}\underline{C}$(cyclopropyl) |
| 3.39 | $CH_3O{-}CH{=}\underline{C}$(cyclopropyl) |
| 3.40 | $C_2H_5{-}CH{=}\underline{C}$(cyclopropyl) |
| 3.41 | $CH_2{=}CH(CH_3)_2\underline{C}$ |

TABLE III-continued

| Cmpd # | R |
|---|---|
| 3.42 | $CH_3CH{=}\underline{C}(CH(CH_3)_2)$ |
| 3.43 | pyridin-3-yl- |
| 3.44 | pyrimidin-2-yl- |
| 3.45 | thien-2-yl- |
| 3.46 | thien-3-yl- |
| 3.47 | 2-naphthyl- |
| 3.48 | 2-furyl- |
| 3.49 | 3-furyl- |
| 3.50 | 2-methylcyclopropyl- |
| 3.51 | 2-ethylcyclopropyl- |
| 3.52 | 2-(n-propyl)cyclopropyl- |
| 3.53 | 2-(n-butyl)cyclopropyl- |
| 3.54 | 2-(iso-butyl)cyclopropyl- |
| 3.55 | 2-(sec-butyl)cyclopropyl- |
| 3.56 | 2-(n-pentyl)cyclopropyl- |
| 3.57 | 2-(iso-pentyl)cyclopropyl- |
| 3.58 | 2-(n-hexyl)cyclopropyl- |
| 3.59 | 2-methoxycyclopropyl- |
| 3.60 | 2-($CH_3O$)cyclopropyl- |
| 3.61 | 2-($CH_3CH_2O$)cyclopropyl- |
| 3.62 | 1-methylcyclopropyl- |
| 3.63 | 2-($CH_2{=}CH$)cyclopropyl- |
| 3.64 | 1-(cyclopropyl)cyclopropyl- |
| 3.65 | 2-(cyclopropyl)cyclopropyl- |
| 3.66 | cyclopropyl-$\underline{C}H_2$ |
| 3.67 | cyclopropyl-CH=$\underline{C}$H |
| 3.68 | 2-((2'-$CH_3$)cyclopropyl) cyclopropyl- |
| 3.69 | 2-(2'-$CH_2{=}CH$) cyclopropylcyclopropyl- |
| 3.70 | 1-Phcyclopropyl- |
| 3.71 | 2-Phcyclopropyl- |
| 3.72 | 1-(2'-ClPh)cyclopropyl- |
| 3.73 | 2-(2'-ClPh)cyclopropyl- |
| 3.74 | 1-(3'-ClPh)cyclopropyl- |
| 3.75 | 2-(3'-ClPh)cyclopropyl- |
| 3.76 | 1-(4'-ClPh)cyclopropyl- |
| 3.77 | 2-(4'-ClPh)cyclopropyl- |
| 3.78 | 1-(2'-FPh)cyclopropyl- |
| 3.79 | 2-(2'-FPh)cyclopropyl- |
| 3.80 | 2-(3'-FPh)cyclopropyl- |
| 3.81 | 2-(4'-FPh)cyclopropyl- |
| 3.82 | 2-(2'-BrPh)cyclopropyl- |
| 3.83 | 2-(3'-BrPh)cyclopropyl- |
| 3.84 | 2-(4'-BrPh)cyclopropyl- |
| 3.85 | 2-(2'-FPh)cyclopropyl- |
| 3.86 | 2-(2'-$CH_3$Ph)cyclopropyl- |
| 3.87 | 2-(3'-$CH_3$Ph)cyclopropyl- |
| 3.88 | 2-(4'-$CH_3$Ph)cyclopropyl- |
| 3.89 | 2-(2'-$CF_3$Ph)cyclopropyl- |
| 3.90 | 2-(3'-$CF_3$Ph)cyclopropyl- |
| 3.91 | 2-(4'-$CF_3$Ph)cyclopropyl- |
| 3.92 | 1-Ph cyclopentyl- |
| 3.93 | 1-Ph cyclohexyl- |
| 3.94 | 2-Ph cyclopentyl- |
| 3.95 | 2-Ph cyclohexyl- |
| 3.96 | 2(2-Ph cyclopropyl)cyclopropyl- |
| 3.97 | 2(1-Ph cyclopropyl)cyclopropyl- |
| 3.98 | Ph$\underline{C}H_2$ |
| 3.99 | 2-ClPh$\underline{C}H_2$ |
| 3.100 | 3-ClPh$\underline{C}H_2$ |
| 3.101 | 4-ClPh$\underline{C}H_2$ |
| 3.102 | 2-$CH_3$Ph$\underline{C}H_2$ |
| 3.103 | 3-$CH_3$Ph$\underline{C}H_2$ |
| 3.104 | 4-$CH_3$Ph$\underline{C}H_2$ |
| 3.105 | 2-($PhCH_2$)cyclopropyl- |
| 3.106 | 2-(2'-$ClPhCH_2$)cyclopropyl- |
| 3.107 | 2-(4'-$ClPhCH_2$)cyclopropyl- |
| 3.108 | 2-(2-$PhCH_2$cyclo propyl)cyclopropyl- |
| 3.109 | 2-(1-$PhCH_2$cyclo-propyl)cyclopropyl- |
| 3.110 | 2-(2-pyridyl)cyclopropyl- |

TABLE III-continued

| Cmpd # | R |
|---|---|

*Compounds 3.02, 3.05 and 3.08 refer to Formula IX, compounds 3.03 and 3.06 refer to Formula X, and the remainder of the compounds refer to Formula VIII. Points of attachment of each substituent to the remainder of the molecule (where not obvious) are indicated by underlining.

VIII

IX

X

Typical compounds encompassed by the present invention of Formula I include those compounds presented in Table IV of Formula XI, XIIi and XIII where X=H, and one of $R_1$ or $R_2$ or $R_3$ or $R_4$ is not H and n=0 or 1, m=0 or 1 and n+m=0 or 1.

TABLE IV

| Cmpd# | R | Formula | n | m | $R_1$ | $R_2$ | $R_3$ | $R_4$ |
|---|---|---|---|---|---|---|---|---|
| 4.01 | Ph- | XI | 0 | 0 | CN | H | H | H |
| 4.02 | Ph- | XII | 0 | 0 | CN | H | H | H |
| 4.03 | Ph- | XIII | 0 | 0 | CN | H | H | H |
| 4.04 | 4-Cl(Ph)- | XI | 0 | 0 | CN | H | H | H |
| 4.05 | 4-Cl(Ph)- | XII | 0 | 0 | CN | H | H | H |
| 4.06 | 4-Cl(Ph)- | XIII | 0 | 0 | CN | H | H | H |
| 4.07 | 2-F(Ph)- | XI | 0 | 0 | CN | H | H | H |
| 4.08 | 4-$CH_3$(Ph)- | XI | 0 | 0 | CN | H | H | H |
| 4.09 | 4-$CH_3O$(Ph)- | XI | 0 | 0 | CN | H | H | H |
| 4.10 | 2,4-Cl(Ph)- | XI | 0 | 0 | CN | H | H | H |
| 4.11 | $\underline{C}H_3$ | XI | 0 | 0 | CN | H | H | H |
| 4.12 | $CH_3\underline{C}H_2$ | XI | 0 | 0 | CN | H | H | H |
| 4.13 | cyclopropyl- | XI | 0 | 0 | CN | H | H | H |
| 4.14 | pyridin-2-yl | XI | 0 | 0 | CN | H | H | H |
| 4.15 | Ph(cyclopropyl)- | XI | 0 | 0 | CN | H | H | H |
| 4.16 | Ph- | XI | 0 | 0 | $CO_2Et$ | H | H | H |
| 4.17 | Ph- | XII | 0 | 0 | $CO_2Et$ | H | H | H |
| 4.18 | Ph- | XIII | 0 | 0 | $CO_2Et$ | H | H | H |
| 4.19 | 4-Cl(Ph)- | XI | 0 | 0 | $CO_2Et$ | H | H | H |
| 4.20 | 2-F(Ph)- | XI | 0 | 0 | $CO_2Et$ | H | H | H |
| 4.21 | 4-$CH_3$(Ph)- | XI | 0 | 0 | $CO_2Et$ | H | H | H |
| 4.22 | 4-$CH_3O$(Ph)- | XI | 0 | 0 | $CO_2Et$ | H | H | H |
| 4.23 | 2,4-Cl(Ph)- | XI | 0 | 0 | $CO_2Et$ | H | H | H |
| 4.24 | $\underline{C}H_3$ | XI | 0 | 0 | $CO_2Et$ | H | H | H |
| 4.25 | $CH_3\underline{C}H_2$ | XI | 0 | 0 | $CO_2Et$ | H | H | H |
| 4.26 | cyclopropyl- | XI | 0 | 0 | $CO_2Et$ | H | H | H |
| 4.27 | pyridin-2-yl- | XI | 0 | 0 | $CO_2Et$ | H | H | H |
| 4.28 | Ph(cyclopropyl)- | XI | 0 | 0 | $CO_2Et$ | H | H | H |
| 4.29 | Ph- | XI | 0 | 0 | H | CN | H | H |
| 4.30 | Ph- | XII | 0 | 0 | H | CN | H | H |
| 4.31 | Ph- | XIII | 0 | 0 | H | CN | H | H |
| 4.32 | 4-Cl(Ph)- | XI | 0 | 0 | H | CN | H | H |
| 4.33 | 4-Cl(Ph)- | XII | 0 | 0 | H | CN | H | H |
| 4.34 | 4-Cl(Ph)- | XIII | 0 | 0 | H | CN | H | H |
| 4.35 | 2-F(Ph)- | XI | 0 | 0 | H | CN | H | H |
| 4.36 | 4-$CH_3$(Ph)- | XI | 0 | 0 | H | CN | H | H |
| 4.37 | 4-$CH_3O$(Ph)- | XI | 0 | 0 | H | CN | H | H |
| 4.38 | 2,4-Cl(Ph)- | XI | 0 | 0 | H | CN | H | H |
| 4.39 | $\underline{C}H_3$ | XI | 0 | 0 | H | CN | H | H |
| 4.40 | $CH_3\underline{C}H_2$ | XI | 0 | 0 | H | CN | H | H |
| 4.41 | cyclopropyl- | XI | 0 | 0 | H | CN | H | H |
| 4.42 | pyridin-2-yl- | XI | 0 | 0 | H | CN | H | H |
| 4.43 | Ph(cyclopropyl)- | XI | 0 | 0 | H | CN | H | H |
| 4.44 | Ph- | XI | 0 | 0 | H | $CO_2Et$ | H | H |
| 4.45 | Ph- | XII | 0 | 0 | H | $CO_2Et$ | H | H |
| 4.46 | Ph- | XIII | 0 | 0 | H | $CO_2Et$ | H | H |
| 4.47 | 4-Cl(Ph)- | XI | 0 | 0 | H | $CO_2Et$ | H | H |
| 4.48 | 4-Cl(Ph)- | XII | 0 | 0 | H | $CO_2Et$ | H | H |
| 4.49 | 4-Cl(Ph)- | XIII | 0 | 0 | H | $CO_2Et$ | H | H |
| 4.50 | 2-F(Ph)- | XI | 0 | 0 | H | $CO_2Et$ | H | H |
| 4.51 | 4-$CH_3$(Ph)- | XI | 0 | 0 | H | $CO_2Et$ | H | H |
| 4.52 | 4-$CH_3O$(Ph)- | XI | 0 | 0 | H | $CO_2Et$ | H | H |
| 4.53 | 2,4-Cl(Ph)- | XI | 0 | 0 | H | $CO_2Et$ | H | H |
| 4.54 | $\underline{C}H_3$ | XI | 0 | 0 | H | $CO_2Et$ | H | H |
| 4.55 | $CH_3\underline{C}H_2$ | XI | 0 | 0 | H | $CO_2Et$ | H | H |
| 4.56 | cyclopropyl- | XI | 0 | 0 | H | $CO_2Et$ | H | H |
| 4.57 | pyridin-2-yl | XI | 0 | 0 | H | $CO_2Et$ | H | H |
| 4.58 | Ph(cyclopropyl)- | XI | 0 | 0 | H | $CO_2Et$ | H | H |
| 4.59 | Ph- | XI | 0 | 0 | H | H | H | CN |
| 4.60 | Ph- | XII | 0 | 0 | H | H | H | CN |
| 4.61 | Ph- | XIII | 0 | 0 | H | H | H | CN |
| 4.62 | 4-Cl(Ph)- | XI | 0 | 0 | H | H | H | CN |
| 4.63 | 4-Cl(Ph)- | XI | 0 | 0 | H | H | H | CN |
| 4.64 | 4-Cl(Ph)- | XI | 0 | 0 | H | H | H | CN |
| 4.65 | 2-F(Ph)- | XI | 0 | 0 | H | H | H | CN |
| 4.66 | 4-$CH_3$(Ph)- | XI | 0 | 0 | H | H | H | CN |
| 4.67 | 4-$CH_3O$(Ph)- | XI | 0 | 0 | H | H | H | CN |
| 4.68 | 2,4-Cl(Ph)- | XI | 0 | 0 | H | H | H | CN |
| 4.69 | $\underline{C}H_3$ | XII | 0 | 0 | H | H | H | CN |
| 4.70 | $CH_3\underline{C}H_2$ | XIII | 0 | 0 | H | H | H | CN |
| 4.71 | cyclopropyl- | XI | 0 | 0 | H | H | H | CN |
| 4.72 | pyridin-2-yl | XII | 0 | 0 | H | H | H | CN |
| 4.73 | Ph(cyclopropyl)- | XIII | 0 | 0 | H | H | H | CN |
| 4.74 | Ph- | XI | 0 | 0 | H | H | H | $CO_2Et$ |
| 4.75 | Ph- | XII | 0 | 0 | H | H | H | $CO_2Et$ |
| 4.76 | Ph- | XIII | 0 | 0 | H | H | H | $CO_2Et$ |
| 4.77 | 4-Cl(Ph)- | XI | 0 | 0 | H | H | H | $CO_2Et$ |

TABLE IV-continued

| Cmpd# | R | Formula | n | m | $R_1$ | $R_2$ | $R_3$ | $R_4$ |
|---|---|---|---|---|---|---|---|---|
| 4.78 | 2-F(Ph)- | XI | 0 | 0 | H | H | H | $CO_2Et$ |
| 4.79 | 4-$CH_3$(Ph)- | XI | 0 | 0 | H | H | H | $CO_2Et$ |
| 4.80 | 4-$CH_3O$(Ph)- | XI | 0 | 0 | H | H | H | $CO_2Et$ |
| 4.81 | 2,4-Cl(Ph)- | XI | 0 | 0 | H | H | H | $CO_2Et$ |
| 4.82 | $\underline{C}H_3$ | XI | 0 | 0 | H | H | H | $CO_2Et$ |
| 4.83 | $CH_3\underline{C}H_2$ | XI | 0 | 0 | H | H | H | $CO_2Et$ |
| 4.84 | cyclopropyl- | XI | 0 | 0 | H | H | H | $CO_2Et$ |
| 4.85 | pyridin-2-yl- | XI | 0 | 0 | H | H | H | $CO_2Et$ |
| 4.86 | Ph(cyclopropyl)- | XI | 0 | 0 | H | H | H | $CO_2Et$ |
| 4.87 | Ph- | XI | 0 | 1 | CN | H | H | H |
| 4.88 | Ph- | XII | 0 | 1 | CN | H | H | H |
| 4.89 | Ph- | XIII | 0 | 1 | CN | H | H | H |
| 4.90 | 4-Cl(Ph)- | XI | 0 | 1 | CN | H | H | H |
| 4.91 | 2-F(Ph)- | XI | 0 | 1 | CN | H | H | H |
| 4.92 | 4-$CH_3$(Ph)- | XI | 0 | 1 | CN | H | H | H |
| 4.93 | 4-$CH_3O$(Ph)- | XI | 0 | 1 | CN | H | H | H |
| 4.94 | 2,4-Cl(Ph)- | XI | 0 | 1 | CN | H | H | H |
| 4.95 | $\underline{C}H_3$ | XI | 0 | 1 | CN | H | H | H |
| 4.96 | $CH_3\underline{C}H_2$ | XI | 0 | 1 | CN | H | H | H |
| 4.97 | cyclopropyl- | XI | 0 | 1 | CN | H | H | H |
| 4.98 | $(CH_3)_3\underline{C}$ | XI | 0 | 1 | CN | H | H | H |
| 4.99 | pyridin-2-yl- | XI | 0 | 1 | CN | H | H | H |
| 4.100 | Ph(cyclopropyl)- | XI | 0 | 1 | CN | H | H | H |
| 4.101 | Ph- | XI | 0 | 1 | $CO_2Et$ | H | H | H |
| 4.102 | Ph- | XII | 0 | 1 | $CO_2Et$ | H | H | H |
| 4.103 | Ph- | XIII | 0 | 1 | $CO_2Et$ | H | H | H |
| 4.104 | 4-Cl(Ph)- | XI | 0 | 1 | $CO_2Et$ | H | H | H |
| 4.105 | 2-F(Ph)- | XI | 0 | 1 | $CO_2Et$ | H | H | H |
| 4.106 | 4-$CH_3$(Ph)- | XI | 0 | 1 | $CO_2Et$ | H | H | H |
| 4.107 | 4-$CH_3O$(Ph)- | XI | 0 | 1 | $CO_2Et$ | H | H | H |
| 4.108 | 2,4-Cl(Ph)- | XI | 0 | 1 | $CO_2Et$ | H | H | H |
| 4.109 | $\underline{C}H_3$ | XI | 0 | 1 | $CO_2Et$ | H | H | H |
| 4.110 | $CH_3\underline{C}H_2$ | XI | 0 | 1 | $CO_2Et$ | H | H | H |
| 4.111 | cyclopropyl- | XI | 0 | 1 | $CO_2Et$ | H | H | H |
| 4.112 | pyridin-2-yl- | XI | 0 | 1 | $CO_2Et$ | H | H | H |
| 4.113 | Ph(cyclopropyl)- | XI | 0 | 1 | $CO_2Et$ | H | H | H |
| 4.114 | Ph- | XI | 0 | 1 | H | CN | H | H |
| 4.115 | Ph- | XII | 0 | 1 | H | CN | H | H |
| 4.116 | Ph- | XIII | 0 | 1 | H | CN | H | H |
| 4.117 | 4-Cl(Ph)- | XI | 0 | 1 | H | CN | H | H |
| 4.118 | 2-F(Ph)- | XI | 0 | 1 | H | CN | H | H |
| 4.119 | 4-$CH_3$(Ph)- | XI | 0 | 1 | H | CN | H | H |
| 4.120 | 4-$CH_3O$(Ph)- | XI | 0 | 1 | H | CN | H | H |
| 4.121 | 2,4-Cl(Ph)- | XI | 0 | 1 | H | CN | H | H |
| 4.122 | $\underline{C}H_3$ | XI | 0 | 1 | H | CN | H | H |
| 4.123 | $CH_3\underline{C}H_2$ | XI | 0 | 1 | H | CN | H | H |
| 4.124 | cyclopropyl- | XI | 0 | 1 | H | CN | H | H |
| 4.125 | pyridin-2-yl- | XI | 0 | 1 | H | CN | H | H |
| 4.126 | Ph(cyclopropyl)- | XI | 0 | 1 | H | CN | H | H |
| 4.127 | Ph- | XI | 0 | 1 | H | $CO_2Et$ | H | H |
| 4.128 | Ph- | XII | 0 | 1 | H | $CO_2Et$ | H | H |
| 4.129 | Ph- | XIII | 0 | 1 | H | $CO_2Et$ | H | H |
| 4.130 | 4-Cl(Ph)- | XI | 0 | 1 | H | $CO_2Et$ | H | H |
| 4.131 | 2-F(Ph)- | XI | 0 | 1 | H | $CO_2Et$ | H | H |
| 4.132 | 4-$CH_3$(Ph)- | XI | 0 | 1 | H | $CO_2Et$ | H | H |
| 4.133 | 4-$CH_3O$(Ph)- | XI | 0 | 1 | H | $CO_2Et$ | H | H |
| 4.134 | 2,4-Cl(Ph)- | XI | 0 | 1 | H | $CO_2Et$ | H | H |
| 4.135 | $\underline{C}H_3$ | XI | 0 | 1 | H | $CO_2Et$ | H | H |
| 4.136 | $CH_3\underline{C}H_2$ | XI | 0 | 1 | H | $CO_2Et$ | H | H |
| 4.137 | cyclopropyl- | XI | 0 | 1 | H | $CO_2Et$ | H | H |
| 4.138 | pyridin-2-yl- | XI | 0 | 1 | H | $CO_2Et$ | H | H |
| 4.139 | Ph(cyclopropyl)- | XI | 0 | 1 | H | $CO_2Et$ | H | H |
| 4.140 | Ph- | XI | 0 | 1 | H | H | H | CN |
| 4.141 | Ph- | XII | 0 | 1 | H | H | H | CN |
| 4.142 | Ph- | XIII | 0 | 1 | H | H | H | CN |
| 4.143 | 4-Cl(Ph)- | XI | 0 | 1 | H | H | H | CN |
| 4.144 | 2-F(Ph)- | XI | 0 | 1 | H | H | H | CN |
| 4.145 | 4-$CH_3$(Ph)- | XI | 0 | 1 | H | H | H | CN |
| 4.146 | 4-$CH_3O$(Ph)- | XI | 0 | 1 | H | H | H | CN |
| 4.147 | 2,4-Cl(Ph)- | XI | 0 | 1 | H | H | H | CN |
| 4.148 | $\underline{C}H_3$ | XI | 0 | 1 | H | H | H | CN |
| 4.149 | $CH_3\underline{C}H_2$ | XI | 0 | 1 | H | H | H | CN |
| 4.150 | cyclopropyl- | XI | 0 | 1 | H | H | H | CN |
| 4.151 | pyridin-2-yl- | XI | 0 | 1 | H | H | H | CN |
| 4.152 | Ph(cyclopropyl)- | XI | 0 | 1 | H | H | H | CN |
| 4.153 | Ph- | XI | 0 | 1 | H | H | H | $CO_2Et$ |
| 4.154 | Ph- | XII | 0 | 1 | H | H | H | $CO_2Et$ |

TABLE IV-continued

| Cmpd# | R | Formula | n | m | $R_1$ | $R_2$ | $R_3$ | $R_4$ |
|---|---|---|---|---|---|---|---|---|
| 4.155 | Ph- | XIII | 0 | 1 | H | H | H | $CO_2Et$ |
| 4.156 | 4-Cl(Ph)- | XI | 0 | 1 | H | H | H | $CO_2Et$ |
| 4.157 | 2-F(Ph)- | XI | 0 | 1 | H | H | H | $CO_2Et$ |
| 4.158 | 4-$CH_3$(Ph)- | XI | 0 | 1 | H | H | H | $CO_2Et$ |
| 4.159 | 4-$CH_3O$(Ph)- | XI | 0 | 1 | H | H | H | $CO_2Et$ |
| 4.160 | 2,4-Cl(Ph)- | XI | 0 | 1 | H | H | H | $CO_2Et$ |
| 4.161 | $CH_3$ | XI | 0 | 1 | H | H | H | $CO_2Et$ |
| 4.162 | $CH_3CH_2$ | XI | 0 | 1 | H | H | H | $CO_2Et$ |
| 4.163 | cyclopropyl- | XI | 0 | 1 | H | H | H | $CO_2Et$ |
| 4.164 | pyridin-2-yl- | XI | 0 | 1 | H | H | H | $CO_2Et$ |
| 4.165 | Ph(cyclopropyl)- | XI | 0 | 1 | H | H | H | $CO_2Et$ |
| 4.166 | Ph- | XI | 0 | 1 | H | —$CH_2$ | $CH_2$— | H |
| 4.167 | Ph- | XII | 0 | 1 | H | —$CH_2$ | $CH_2$— | H |
| 4.168 | Ph- | XIII | 0 | 1 | H | —$CH_2$ | $CH_2$— | H |
| 4.169 | 4-Cl(Ph)- | XI | 0 | 1 | H | —$CH_2$ | $CH_2$— | H |
| 4.170 | 2-F(Ph)- | XI | 0 | 1 | H | —$CH_2$ | $CH_2$— | H |
| 4.171 | 4-$CH_3$(Ph)- | XI | 0 | 1 | H | —$CH_2$ | $CH_2$— | H |
| 4.172 | 4-$CH_3O$(Ph)- | XI | 0 | 1 | H | —$CH_2$ | $CH_2$— | H |
| 4.173 | 2,4-Cl(Ph)- | XI | 0 | 1 | H | —$CH_2$ | $CH_2$— | H |
| 4.174 | $CH_3$ | XI | 0 | 1 | H | —$CH_2$ | $CH_2$— | H |
| 4.175 | $CH_3CH_2$ | XI | 0 | 1 | H | —$CH_2$ | $CH_2$— | H |
| 4.176 | cyclopropyl- | XI | 0 | 1 | H | —$CH_2$ | $CH_2$— | H |
| 4.177 | $(CH_3)_3C$ | XI | 0 | 1 | H | —$CH_2$ | $CH_2$— | H |
| 4.178 | pyridin-2-yl- | XI | 0 | 1 | H | —$CH_2$ | $CH_2$— | H |
| 4.179 | Ph(cyclopropyl)- | XI | 0 | 1 | H | —$CH_2$ | $CH_2$— | H |
| 4.180 | Ph- | XI | 1 | 0 | CN | H | H | H |
| 4.181 | Ph- | XII | 1 | 0 | CN | H | H | H |
| 4.182 | Ph- | XIII | 1 | 0 | CN | H | H | H |
| 4.183 | 4-Cl(Ph)- | XI | 1 | 0 | CN | H | H | H |
| 4.184 | 2-F(Ph)- | XI | 1 | 0 | CN | H | H | H |
| 4.185 | 4-$CH_3$(Ph)- | XI | 1 | 0 | CN | H | H | H |
| 4.186 | 4-$CH_3O$(Ph)- | XI | 1 | 0 | CN | H | H | H |
| 4.187 | 2,4-Cl(Ph)- | XI | 1 | 0 | CN | H | H | H |
| 4.188 | $CH_3$ | XI | 1 | 0 | CN | H | H | H |
| 4.189 | $CH_3CH_2$ | XI | 1 | 0 | CN | H | H | H |
| 4.190 | Cyclopropyl | XI | 1 | 0 | CN | H | H | H |
| 4.191 | $(CH)_3C$ | XI | 1 | 0 | CN | H | H | H |
| 4.192 | pyridin-2-yl- | XI | 1 | 0 | CN | H | H | H |
| 4.193 | Ph(cyclopropyl)- | XI | 1 | 0 | CN | H | H | H |
| 4.194 | Ph- | XI | 1 | 0 | $CO_2Et$ | H | H | H |
| 4.195 | Ph- | XII | 1 | 0 | $CO_2Et$ | H | H | H |
| 4.196 | Ph- | XIII | 1 | 0 | $CO_2Et$ | H | H | H |
| 4.197 | 4-Cl(Ph)- | XI | 1 | 0 | $CO_2Et$ | H | H | H |
| 4.198 | 2-F(Ph)- | XI | 1 | 0 | $CO_2Et$ | H | H | H |
| 4.199 | 4-$CH_3$(Ph)- | XI | 1 | 0 | $CO_2Et$ | H | H | H |
| 4.200 | 4-$CH_3O$(Ph)- | XI | 1 | 0 | $CO_2Et$ | H | H | H |
| 4.201 | 2,4-Cl(Ph)- | XI | 1 | 0 | $CO_2Et$ | H | H | H |
| 4.202 | $CH_3$ | XI | 1 | 0 | $CO_2Et$ | H | H | H |
| 4.203 | $CH_3CH_2$ | XI | 1 | 0 | $CO_2Et$ | H | H | H |
| 4.204 | cyclopropyl- | XI | 1 | 0 | $CO_2Et$ | H | H | H |
| 4.205 | $(CH_3)_3C$ | XI | 1 | 0 | $CO_2Et$ | H | H | H |
| 4.206 | pyridin-2-yl- | XI | 1 | 0 | $CO_2Et$ | H | H | H |
| 4.207 | Ph(cyclopropyl)- | XI | 1 | 0 | $CO_2Et$ | H | H | H |

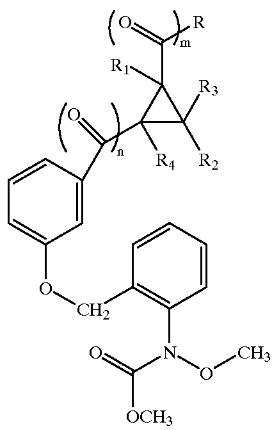

XI

TABLE IV-continued

| Cmpd# | R | Formula | n | m | $R_1$ | $R_2$ | $R_3$ | $R_4$ |
|---|---|---|---|---|---|---|---|---|
| | XII | | | | | | | |
| | XIII | | | | | | | |

As used in Table I to IV Ph is understood to be phenyl.

The compounds of Formula I can be prepared by a variety of synthetic routes. A general overview of synthesis methods for cyclopropanes is described in March, *Advanced Organic Chemistry,* 4th Ed. pp. 866–873 and references therein.

When n and m are both zero, $R_1$ and $R_4$ are hydrogen, and at least one of $R_2$ and $R_3$ is hydrogen, the compounds of formula (I) are prepared in a four step sequence shown in Scheme A.

Scheme A

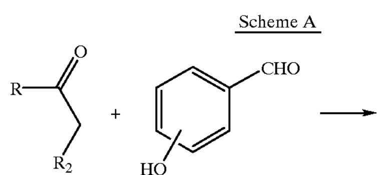

-continued

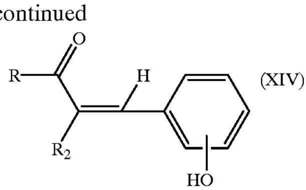

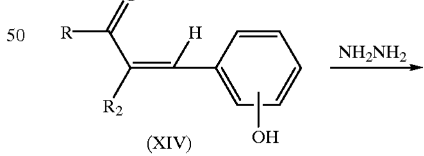

when $R_2$ is H

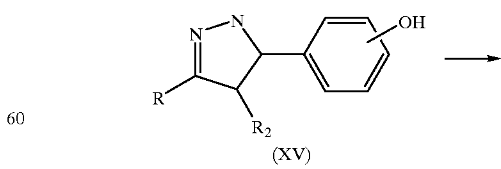

-continued

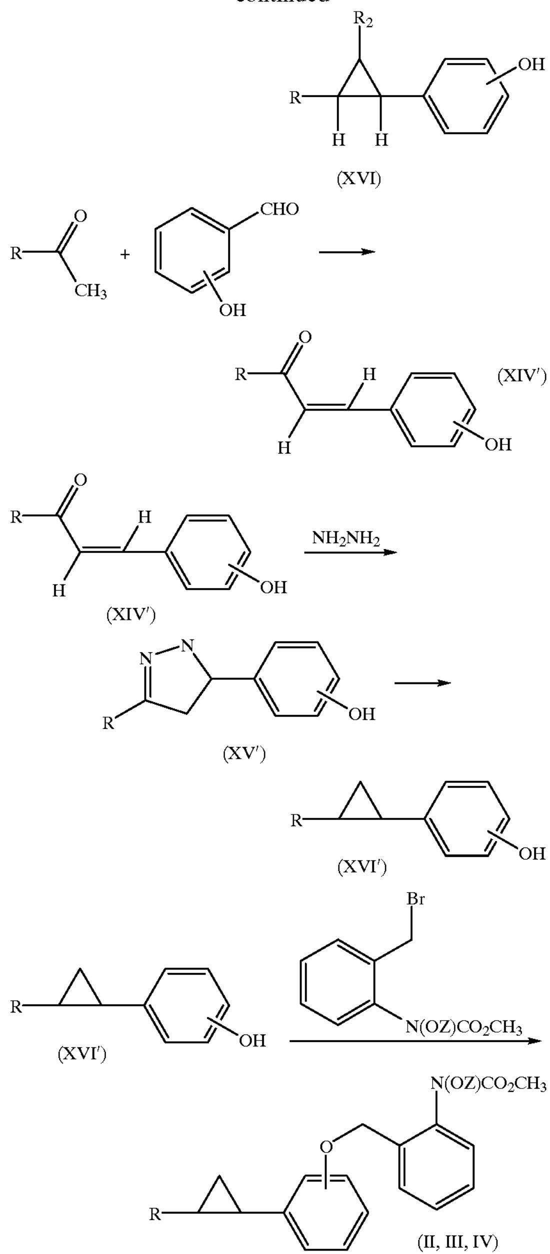

The substituted cyclopropyl phenols XVI are prepared from the pyrazolines XV which are prepared from α,β unsaturated compounds (XIV). These enones can be prepared by conventional condensation techniques. For example *Organic Reactions,* Volume 16 describes the general aldol condensation and specifically the condensation of benzaldehydes with ketones. A hydroxybenzaldehyde is condensed with a ketone, $RCOCH_2R_2$, which when $R_2$=H is a methyl ketone, provides the unsaturated intermediate XIV'. Substituted hydroxybenzaldehyde such as ortho-, meta-, or para-hydroxybenzaldehyde provides three corresponding regioisomeric intermediates XIV and XIV'. A variety of reaction conditions can be employed to prepare the enones XIV and XIV' which are described in *Organic Reactions* Vol 16 pp. 69–85. For example a ketone is dissolved in a hydroxylic solvent (i.e. an hydroxide-containing hydrophilic solvent) such as methanol, ethanol, etc., to which is added dropwise a solution of the hydroxybenzaldehyde in an aqueous basic solution. The bases used can be alkali metal hydroxides, such as potassium or sodium hydroxide and the dropwise addition is conducted from 0° C. to 35° C. preferably at ambient temperature.

The intermediate enones XIV and XIV' are reacted with hydrazine to provide the intermediate XV and XV' pyrazoline. Typical preparation of pyrazolines from unsaturated enones by treatment with hydrazine are described in *Synthetic Commun,* 25(12), 1877–1883 (1995); *JACS* 73, 3840 (1951); *Indian J. Chem Soc Sect B* 98–104 (1992) and J. Indian Chem Soc 643–644 (1993). For example, in JACS 73, 3840 (1951) styryl cyclopropyl ketone is reacted with aqueous hydrazine in 95% ethanol and stirred on a steam bath for 1 hr. which after distillation gave the pyrazoline in 86% yield. Similarly in *Synthetic Commun,* 25(12), 1877–1883 (1995) chalcones were treated with hydrazine monohydrate and stirred at reflux in ethanol and gave the pyrazolines in >90% yield. The intermediate pyrazoline XV' is heated with caustic (NaOH) at 250° C. as described in *Synthetic Commun,* 25(12), and *JACS* 73, 3840 (1951) to provide the cyclopropyl phenols XVI'.

Compounds of Tables 1 of formula II, III and IV are prepared by the alkylation of intermediate cyclopropyl phenols XVI' with the appropriately substituted benzyl bromide as shown in Scheme A. Alkylation of cyclopropyl phenol intermediate XVI' derived from meta-hydroxybenzaldehyde provides compounds of Table 1 of Formula II. Alkylation of intermediate XVI' derived from ortho-hydroxybenzaldehyde provides compounds of Table 1 of Formula III and alkylation of intermediate XVI' derived from para-hydroxybenzaldehyde provides compounds of Table 1 of Formula IV.

The 2-N(OZ)$CO_2CH_3$-benzylbromide, methyl N-(2-bromomethylphenyl)-N-alkoxycarbamate, is prepared as described in both EP619301 and EP704430 in a 4 step sequence as shown in Scheme B. As described in the aforementioned European patent applications o-nitrotoluene is reacted with ammonium chloride in the presence of zinc toprovide N-2-methyl phenyl hydroxylamine (XI) as described in Organic Synthesis Collective Volume III, p.668. The hydroxylamine is acylated with methyl chloroformate to provide the methyl phenyl N-hydroxycarbamate (XII) which is alkylated, for example with dimethylsulfate (R is methyl), to provide (XIII) which is brominated under standard conditions such as N-bromosuccinimide in carbon tetrachloride in the presence of a catalyst such as benzoyl peroxide to afford the intermediate benzylbromide (XIV).

Scheme B

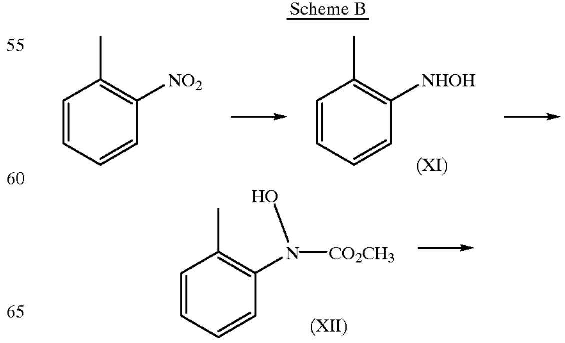

-continued

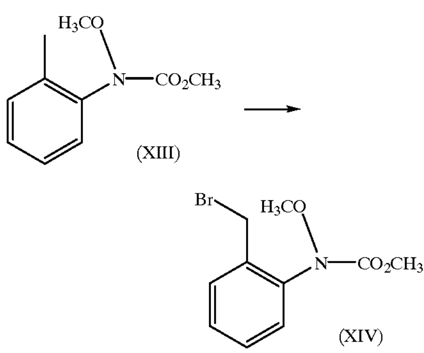

Scheme C describes the preparation of compounds of the formula (I) where $R_1$ and $R_4$ are hydrogen and at least one of $R_2$ and $R_3$ is hydrogen. The α,β unsaturated compounds (XVII) can be prepared by conventional condensation techniques. For example Organic Reactions, Volume 16 describes the general aldol condensation and specifically the condensation of aldehydes with ketones. An aldehyde, for example a substituted benzaldehyde is condensed with an hydroxyphenylketone, $(OH)PHCOCH_2R_2$, which, when $R_2$=H is a methyl ketone, provides the unsaturated intermediate XVII'.

Scheme C

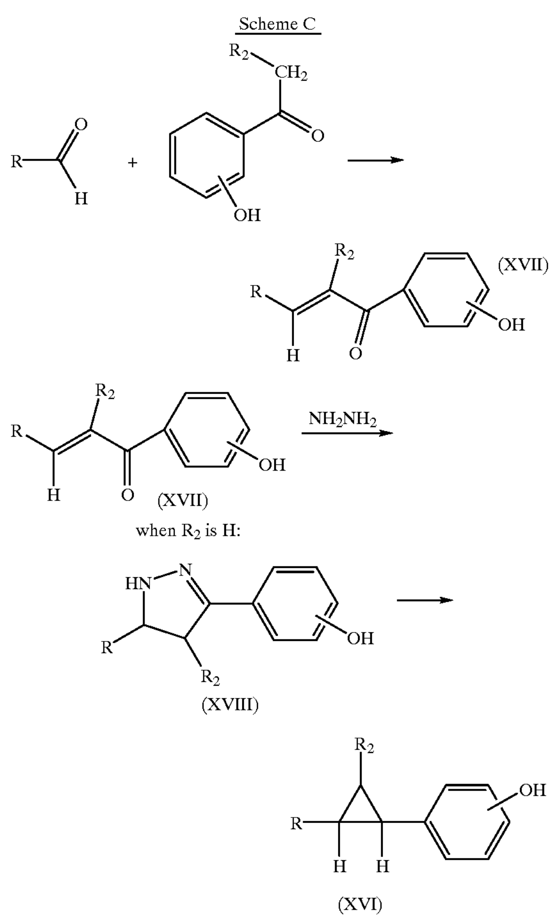

-continued

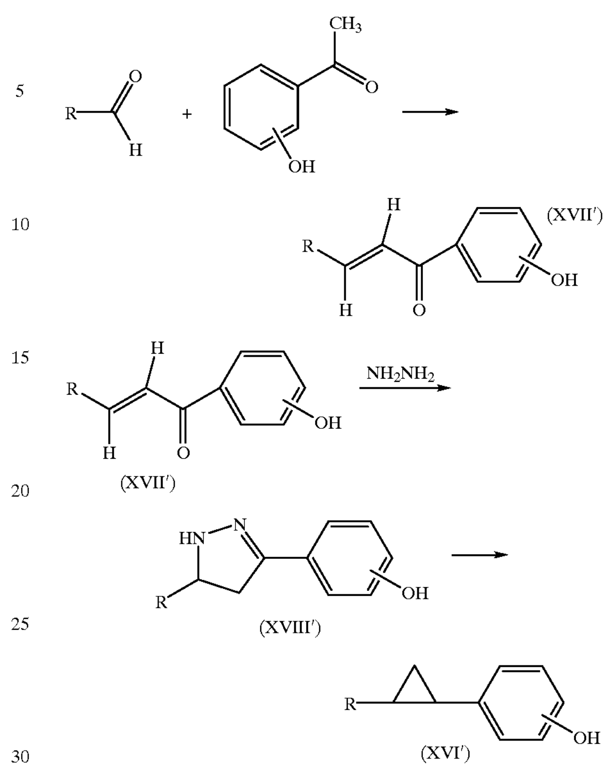

Substituted hydroxyphenylketones provide the three regioisomeric intermediates XVII ($R_2$ is not H) and substituted hydroxyphenylketones such as ortho, meta, or para-hydroxyacetophenone provide three regioisomeric intermediates XVII' where $R_2$=H. The intermediate enones XVII and XVII' are reacted with hydrazine in the same manner as intermediate XIV and XIV' (Scheme A) resulting in the cyclopropyl phenols XVI and XVI'; as described in Scheme C. The cyclopropylphenols XVI' are used to prepare compounds of Table 1 of formula II, III, and IV as described in Scheme A.

When n is zero and m=1 the compounds of formula (I) are prepared in three step sequence shown in Scheme D. The unsaturated intermediate XIV" (scheme D) prepared by conventional condensation techniques from $RCOCH_2R_1$ and a hydroxybenzaldehyde is reacted with a sulfur ylide, prepared from a dimethylsulfoxonium salt in the presence of a base, resulting in the substituted acyl cyclopropyl phenols, XIX. The chemistry of sulfur ylides is described in Trost and Melvin, *Sulfur Ylids,* Academic Press, New York, N.Y. 1975 and in Block, *Reactions of Organosulfur Compounds,* pp. 91–123, Academic Press, New York, N.Y. 1978. Typical reaction conditions for sulfur ylide formation from a dimethylsulfoxonium salt utilizes bases such as hydroxides, metal hydrides and alkoxides in solvents such as dimethoxyethane, dimethylsufoxide and water depending on the base employed. The reactions are conducted from 0 to 20° C. preferably from 10–15° C. and preferably with alkali metal hydroxides in dimethylsulfoxide.

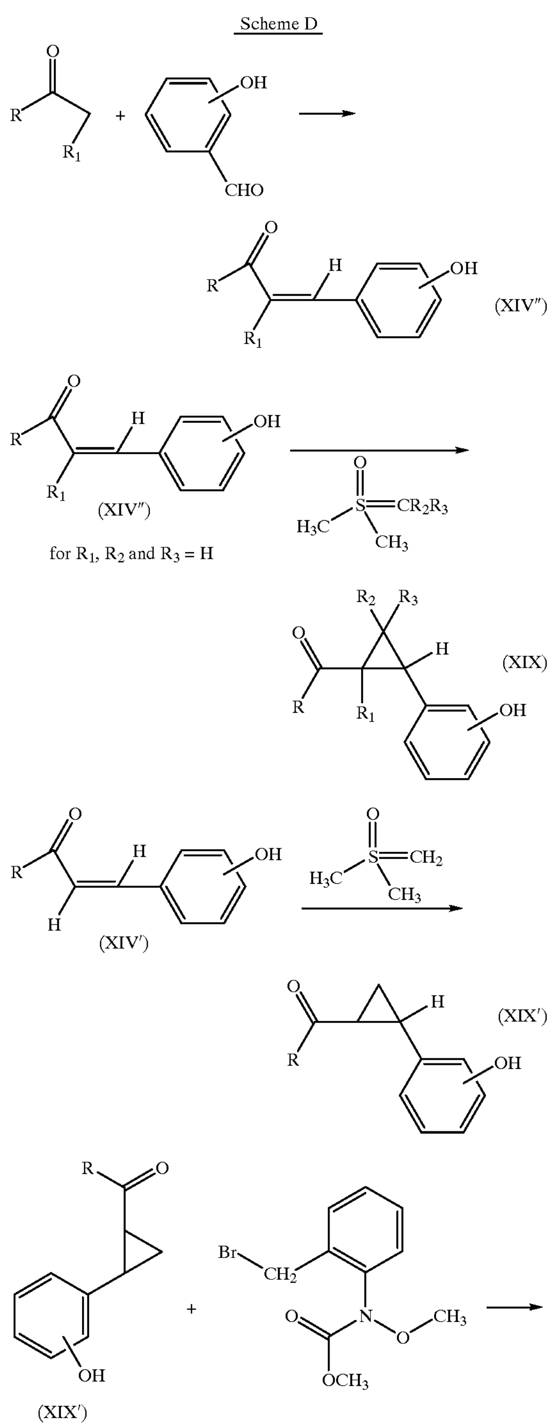

-continued

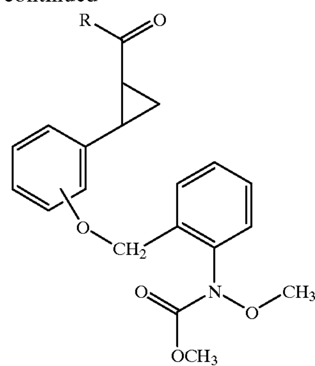

V, VI, VII

The appropriate substituted acyl cyclopropyl phenols XIX' are alkylated with the benzylbromide of Scheme A to provide compounds of formula V, VI and VII of Table 2 and similarly the substituted acyl cyclopropyl phenols XIX provide compounds of formula XI, XII, XIII of Table IV where n=0 and m=1.

When n is 1 and m is zero the compounds of formula (I) are prepared in three step sequence shown in Scheme E. The substituted cyclopropyl phenols XX are prepared from α,β unsaturated compounds XVIIΔ. These enones are reacted with a sulfur ylide, prepared from a dimethylsulfoxonium salt in the presence of a base, resulting in the substituted acyl cyclopropyl phenols XX.

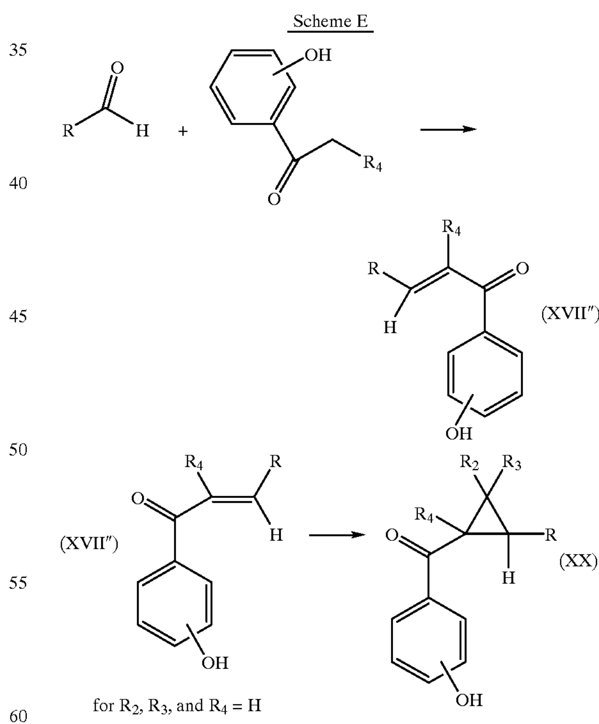

-continued

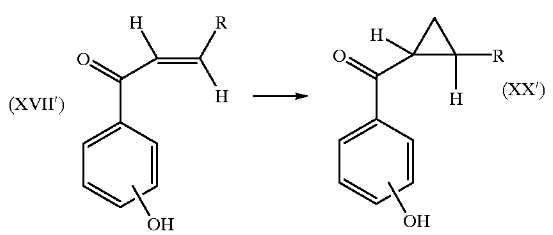

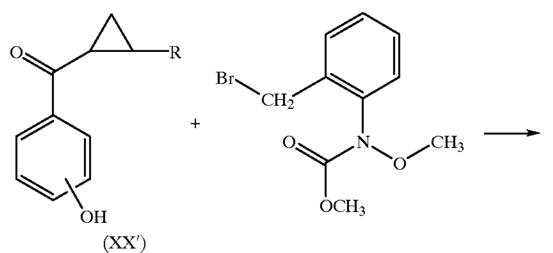

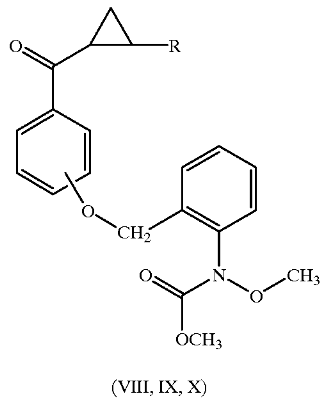

The substituted acyl cyclopropyl phenols XX' are alkylated with the benzylbromide of Scheme a to provide compounds of formula VII, IX and X of Table 3 and similarly the substituted acyl cyclopropyl phenols XX provide compounds of Formula XI, XII, XIII of Table IV where n=1 and m=0.

When n and m are both zero and R is an alkenyl-containing moiety the alkenyl substituted cyclopropylphenols can be prepared from intermediates XIX by Wittig olefination of the acylcyclopropane phenols as shown in Scheme F.

Scheme F

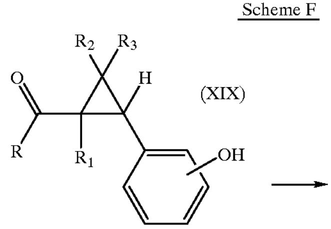

-continued

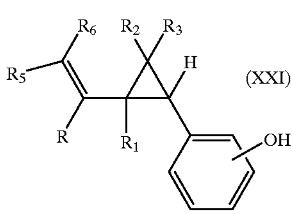

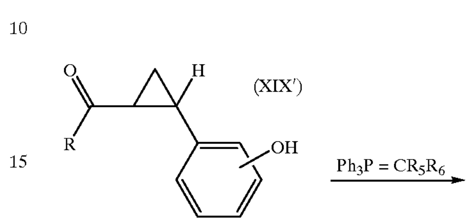

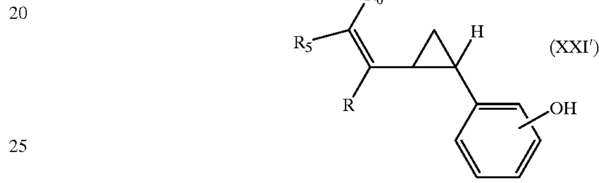

For an overview of the Wittig olefination see March, Advanced Organic Chemistry, 4th, Ed. pp. 956–963 and references therein. For a general review of the Wittig olefination see Cadogan Organophosphorus Reagents in Organic Synthesis, 1979 and Johnson Ylid Chemistry, 1966. Typical reaction conditions for the Wittig reaction from a phosphonium salt utilize bases such as, metal hydrides and alkoxides in solvents such as toluene, THF, ether, dimethoxyethane and ethanol depending on the base employed. The reactions are conducted from 20 to 120° C. preferably from 75 to 120° C. and preferably with alkoxides such as potassium tert-butoxide in THF. The olefinic intermediate XXI' is alkylated with appropriate benzylbromide of Scheme A to provide compounds of Formula II, III and IV of Table 1.

Compounds of formula (I) where $R_2$ and $R_3$ are other than hydrogen and n is 0 or 1 and m is 0 or 1 such that n+m=1 are prepared in three step sequence shown in Scheme G. The substituted cyclopropyl phenols (XXIII) and (XXIV) are prepared from α,β unsaturated compounds as described in Schemes D and E.

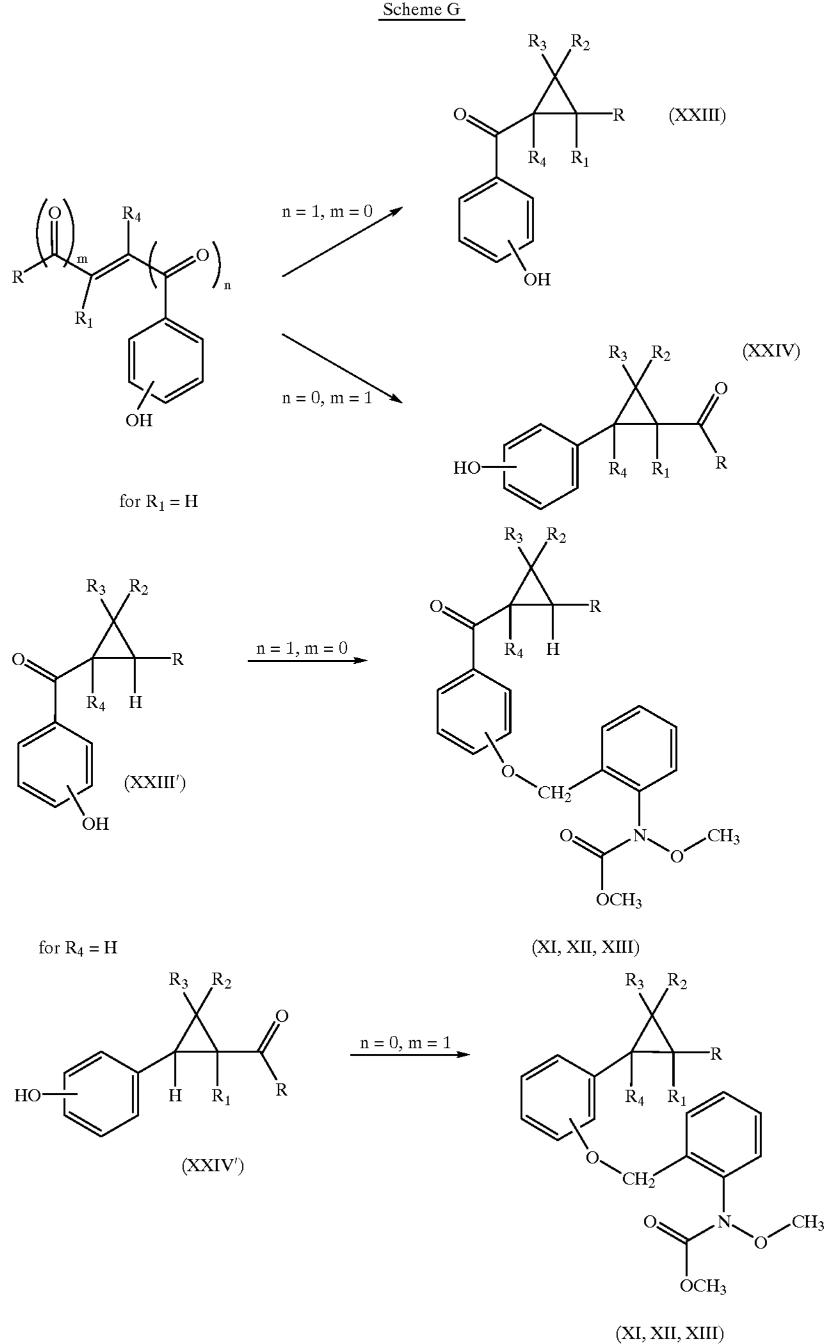

The substituted acyl cyclopropyl phenols XXIII and XXIV are alkylated with appropriate benzylbromide to provide compounds of Formula XI, XII and XIII of Table 4.

Compounds of formula (I) where $R_1$ or $R_4$ are other than hydrogen can also be prepared as in Scheme H where $R_1$ and $R_4$ are electron withdrawing substituents such as cyano and alkoxycarbonyl. The acrylonitriles and acrylate starting materials as shown in scheme H can be prepared by conventional synthetic methods as described in March, Advanced Organic Chemistry, 4th Ed. Acrylonitriles XXV and XXVII are treated as in Schemes C and D with a sulfur ylid to provide cyclopropyl phenols XXVI and XXVIII as is shown in Scheme H ($R_1$ or $R_4$ is cyano). The substituted acyl cyclopropyl phenols XXVI and XXVIIIi are alkylated with the appropriate benzylbromide to provide compounds of Formula XI, XII and XIII of Tables IV where n+m=0.

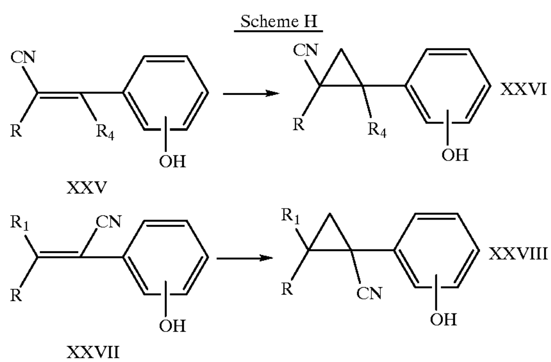

Compounds of formula (I) where n and m are zero and $R_2$ or $R_3$ are other than hydrogen can also be prepared as in Scheme I. A general overview of synthesis methods for olefins and for cyclopropanes utilizing carbenes is described in March, Advanced Organic Chemistry, 4th Ed, pp. 866–872 and the many references therein.

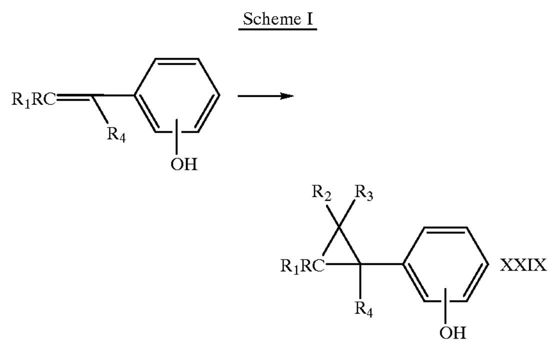

The substituted acyl cyclopropyl phenols XIX is alkylated with the appropriate benzylbromide to provide compounds of Formula IX, XII and XIII of Table IV where n+m=0.

The compounds of this invention can be made according to the the following procedures:

EXAMPLE 1

Preparation of Methyl N-methoxy-N-[2-(3-(2-phenylcyclopropyl) phenoxymethyl) phenyl]carbamate (Compound 1.01, Table 1)

To a 25 ml glass vial equipped with a magnetic stirring bar was charged 0.35 g (0.00165 moles) of 1-(3-hydroxyphenyl)-2-phenylcyclopropane, 10 mls of dry N,N-dimethylformamide, and 0.07 g (0.00165 moles) of powdered sodium hydroxide. To this solution was added 0.6 g (0.00165 moles) of methyl N-2-bromomethylphenyl-N-methoxycarbamate (75% pure) in one portion. The vial was capped and stirred overnight at ambient temperature, The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 0.5 g of the crude produce as an dark brown oil. This material was chromatographed on a mixed bed of neutral alumina and silica gel with 50% ethyl acetate, 50% hexane. The pure fractions were combined, and concentrated under reduced pressure with a rotary evaporator to afford 0.25 g of the title compound, Methyl N-methoxy-N-[2-(3-(2-phenylcyclopropyl)phenoxy)methyl phenyl]carbamate as a viscous pale yellow oil in a 37% isolated yield.

$^1$H NMR ($CDCl_3$, tms=0 ppm) 1.2(m,2H); 2.1(m,2H); 3.7(s,3H); 3.8(s,3H); 5.1(s,2H); 6.7(m,3H); 7.1–7.4(m,6H); 7.5(m,3H); 7.7(m,1H).

Preparation of 1-(3-hydroxyphenyl)-2-phenylcyclopropane

To a 250 ml round bottom flask equipped with nitrogen inlet, thermometer, and reflux condenser was charged 3.5 g (0.0147 moles) of 5-(3-hydroxyphenyl)-3-phenyl-2-pyrazoline, and 2.2 g (0.1 moles) of powdered sodium hydroxide. The two solids were mixed thoroughly, then heated slowly to 250° C., under a rapid steam of nitrogen. The reaction mixture was heated continuously at 250° C. for a total of 2 hours, then cooled to ambient temperature. The resulting residue was the dissolved in 200 mls of water, then acidified to pH 2 with 1N aqueous hydrochloric acid. The acidic solution was extracted with 3×100 mls of ethyl ether, and the ether extract was washed with 2×100 mls of water, and 100 mls of saturated aqueous sodium chloride solution. The ether extract was the dried over anhydrous magnesium sulfate, filtered and concentrated to dryness under reduced pressure with a rotary evaporator at 45° C. The resulting crude product was chromatographed on silica gel with a 15% ethyl acetate, 85% hexane mobile phase. The pure fractions were combined and concentrated under reduced pressure on a rotary evaporator to afford 1.8 g of the title compound 1-(3-hydroxyphenyl)-2-phenyl-cyclopropane as a pale yellow liquid in a 58% yield. $^1$H NMR ($CDCl_3$, tms=0 ppm) 1.4(t,2H); 2.2(m,2H); 5.5(s,1H); 6.5–6.8(m,3H); 3.1–3.4(m,6H).

Preparation of 5-(3-hydroxyphenyl)-3-phenyl-2-pyrazoline

To a 250 ml round bottom flask equipped with magnetic stirrer and reflux condenser was charged 3.2 g (0.0143 moles) of 3-hydroxychalcone, 50 mls of ethanol and 0.7 g (0.0143 moles) of hydrazine monohydrate. The reaction was refluxed for a total of 2 hours, after which it was cooled to ambient temperature. The resulting solid was collected by vacuum filtration, washed with hexane, and dried in vacuuo at 40° C. overnight to afford 3.4 g of the title compound, 3-phenyl-5-(3-hydroxyphenyl)-2-pyrazoline as a tan solid in a 99% isolated yield.

$^1$H NMR ($CDCl_3$, tms=0 ppm) 3.0(dd,1H); 3.5(dd,1H); 2.9(t,1H); 6.5-3.0(m,3H); 3.1(m,1H); 3.3–3.5(m,3H); 3.6 (m,2H); 9.0(bs,1H).

EXAMPLE 2

Preparation of Methyl N-methoxy-N-[2-(3-(2-cyclopropylcyclopropyl) phenoxymethyl) phenyl] carbamate (Compound 1.34, Table 1)

To a 25 ml glass vial equipped with a magnetic stirring bar was charged 0.30 g (0.00165 moles ) of 1-(3-hydroxyphenyl)-2-cyclopropylcyclopropane, 10 mls of dry N,N-dimethylformamide, and 0.07 g (0.00165 moles) of powered sodium hydroxide. To this solution was added 0.6 g (0.00165 moles) of methyl N-2-bromomethylphenyl-N-methoxycarbamate (75% pure) in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 0.6 g of the crude product as an dark brown oil. This material was chromatographed on a mixed bed of neutral alumina and silica gel with 50% ethyl acetate, 50% hexane. The pure fractions were combined, and concentrated under reduced pressure with a rotary evaporator to afford 0.25 g of the title compound, Methyl N-methoxy-N-[2-(3-(2-cyclopropylcyclopropyl) phenoxymethyl)-phenyl] carbamate as a viscous yellow oil in a 41% isolated yield.

300 MHz $^1$H NMR ($CDCl_3$, tms=0 ppm)) 0.2(m,2H); 0.4(m,1H); 0.7(m,2H); 0.8–0.9(m,2H); 1.0(m,1H); 1.2(m, 1H); 3.7(s,3H); 3.8(s,3H); 5.1(s,2H); 6.6–7.0(m,4H); 7.2(m, 1H); 7.6(m,2H); 7.7(m,1H).

Preparation of 2-cyclopropyl-1-(3-hydroxyphenyl) cyclopropane

To a 250 ml round bottom flask equipped with nitrogen inlet, thermometer, and reflux condenser was charged 5.0 g (0.0246 moles) of 3-cyclopropyl-5-(3-hydroxyphenyl)-2-pyrazoline, and 5.0 g of powdered sodium hydroxide (0.125 moles). The two solids were mixed thoroughly, then heated slowly to 250° C., under a rapid steam of nitrogen. The reaction mixture was heated continuously at 250° C. for a total of 2 hours, then cooled to ambient temperature. The resulting residue was the dissolved in 200 mls of water, then acidified to pH 2 with 1N aqueous hydrochloric acid. The acidic solution was extracted with 3×100 mls of ethyl ether, and the ether extract was washed with 2×100 mls of water, and 100 mls of saturated aqueous sodium chloride solution. The ether extract was the dried over anhydrous magnesium sulfate, filtered and concentrated to dryness under reduced pressure with a rotary evaporator at 45° C. The resulting crude product was chrmoatographed on silica gel with a 15% ethyl acetate, 85% hexane mobile phase. The pure fractions were combined and concentrated under reduced pressure on a rotary evaporator to afford 2.9 g of the title compound 1-(3-hydroxyphenyl)-2-cyclopropyl cyclopropane as a pale yellow liquid at a 68% yield.

200 MHz $^1$H NMR ($CDCl_3$, tms=0 ppm) 0.2(m,2H); 0.4(m,2H); 0.7(m,2H); 0.8–1.0(m,2H); 1.5(m,1H); 5.4(bs, 1H); 6.5(m,1H); 6.7(m,2H); 7.1(t,1H).

Preparation of 3-cyclopropyl-5-(3-hydroxyphenyl)-2-pyrazoline

To a 500 ml round bottom flask equipped with magnetic stirrer and reflux condenser was charged 13.2 g (0.0702 moles) of cyclopropyl 3-hydroxystyrylketone 150 mls of water and 3.5 g (0.0702 moles) of hydrazine monohydrate. The reaction was refluxed for a total of 2 hours, after which it was cooled and diluted with an additional 200 mls of water. The resulting solid was collected by vacuum filtration, washed with water and hexane, and dried in vacuuo at 40° C. overnight to afford 9.6 g of 3-cyclopropyl-5-(3-hydroxyphenyl)-2-pyrazoline as a tan solid at a 68% isolated yield.

Preparation of cyclopropyl 3-hydroxystyrylketone

To a 500 ml round bottom flask equipped with magnetic stirrer and side arm addition funnel was charged 6.8 g (0.08 moles) of cyclopropylmethyl ketone and 100 ml of absolute ethanol. 3-hydroxybenzaldehyde (9.8 g 0.08 moles) and 6.4 g of 86% potassium hydroxide (0.1 moles) were dissolved in 100 ml of water and added dropwise to the stirring solution of cyclopropylmethyl ketone, at room temperature. The reaction was stirred at ambient temperature overnight, then poured into 250 mls of water, and acidified to pH 2 with 1N aqueous hydrochloric acid, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 13.7 g (91% yield) of product, cyclopropyl 3-hydroxystyrylketone, as an amber oil.

EXAMPLE 3

Preparation of MethylN-methoxy-N-[2-(3-(2-benzoylcyclopropyl) phenoxymethyl) phenyl]carbamate. (Compound 2.01, Table 4)

To a 25 ml glass vial equipped with a magnetic stirring bar was charged 1.0 g (0.00504 moles) of 2-benzoyl-1-(3-hydroxyphenyl)cyclopropane, 20 mls of dry N,N-dimethylformamide, and 0.2 g (0.00504 moles) of powdered sodium hydroxide. To this solution was added 2.0 g (0.0054 moles) of methyl N-(2-bromomethylphenyl)-N-alkoxycarbamate (75% pure) in one portion. The vial was capped and stirred overnight at ambient temperature. The reaction mixture was then poured into 100 mls of water, and extracted with 3×100 mls of ethyl ether. The ether extract was then washed with 2×100 mls of water and 100 mls of saturated aqueous sodium chloride solution. The ether extract was then dried over anhydrous magnesium sulfate, filtered, and concentrated under reduced pressure with a rotary evaporator at 45° C. to afford 2.5 g of the crude product as an dark brown oil. This material was chromatographed on a mixed bed of neutral alumina and silica gel with 50% ethyl acetate, 50% hexane. The pure fractions were combined, and concentrated under reduced pressure with a rotary evaporator to afford 1.2 g (55% yield) of the tital compound, Methyl N-methoxy-N-[2-(3-(2-benzoylcyclopropyl)phenoxymethyl)phenyl]carbamate as a viscous pale yellow oil. 300 MHz $^1$H NMR ($CDCl_3$, tms=0 ppm) 1.6(m,1H); 1.9(m,1H); 2.7(m,1H); 2.9(m,1H); 3.7(s, 3H); 3.8(s,3H); 5.1(s,2H); 6.7(m,3H); 7.2(m,2H); 7.3–7.7 (m,6H); 8.8(m,2H).

Preparation of 2-benzoyl-1-(3-hydroxyphenyl)cyclopropane

To a 250 ml round bottom flask equipped with magnetic stirrer, nitrogen inlet, thermometer and addition funnel was charged 0.71 g (0.0178 moles) of 60% sodium hydroxide (oil suspension) and 50 mls of anhydrous DMSO. With stirring, under a nitrogen atmosphere, the trimethylsulfoxonium iodide (3.9 g, 0.0178 moles) was added in one portion, and the reaction was stirred at ambient temperature for 30 minutes. The mixture was then cooled to 15° C., and a solution of 3-hydroxychalcone (2.0 g, 0.0089 moles) was added dropwide in 10 mls of DMSO. The reaction was stirred for 1 hour at 15.10 C., then allowed to warm to ambient temperature, and stirred for an additional 16 hours. The reaction mixture was the quenched with 100 mls of 0.1N HCl, and extracted with 3×100 mls of ethyl ether. The combined ether extracts were washed successively with 2×100 mls of water, and 100 mls of saturated aqueous sodium chloride solution. The ether extract was then dried over anhydrous magnesium sulfate, filtered and concentrated to dryness under reduced pressure with a rotary evaporator at 45° C. to afford 2.1 g of the tital compound, 2-benzoyl-1-(3-hydroxyphenyl)cyclopropane, as a thick yellow oil. 100% crude yield.

300 MHz $^1$H NMR ($CDCl_3$, tms=0 ppm) 1.5(m,1H); 1.9(m,1H); 2.6(m,1H); 2.9(m,1H); 5.7(bs,1H); 6.8(m,3H); 3.1(t,1H); 3.4(m,2H); 3.5(d,1H); 8.0(d,2H).

EXAMPLE 4

Numerous compounds of this invention were tested for fungicidal activity in vivo against the diseases described below. The compounds were dissolved in a 2:1:1 mixture of water, acetone and methanol (by volume), sprayed onto the plants, allowed to dry (two hours) and then the plants were inoculated with fungal spores. Each test utilized control plants which were sprayed with the water, acetone and methanol mixture and inoculated. The remainder of the technique of each of the tests is given below along with the results for various compounds described herein by the Compound # against the various fungi at a dose of 300 gams per hectare. The results are reported as percent disease control, compared to the control wherein one hundred was rated as total disease control and zero as no disease control. The application of the fungi to the test plants was as follows:

Wheat Leaf Rust (WLR)

*Puccinia recondita* (f. sp. tritici) was cultured on 7 day old wheat (cultivar Fielder) over a 12 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per flat of twenty 2 inch square pots of 7 day old Fielder wheat. After waiting for at least 15 minutes for the oil to evaporate from the wheat leaves, the plants were placed in a dark mist chamber (18–20° C. and 100% relative humidity) for 24 hours. The plants were then put in the greenhouse for the latent period and scored after 12 days for disease levels. For protective tests the plants are inoculated one day after spraying the plants with the fungicide compounds.

Wheat Leaf Blotch (SNW)

Cultures of *Septoria nodorum* was maintained on Czapek-Dox V-8 juice agar plates in an incubator 20° C. with alternating periods of 12 hours of light and 12 hours of darkenss for 3 weeks. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one week oil Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. tritici) was cultured on wheat seedlings in a controlled temperature room at 18° C. Mildew spores were shaken from the culture plants onto 7 day old wheat seedlings which had been previously sprayed with the fungicide compound. The inoculated seedlings were kept in a controlled temperature room at 18° C. and subirrigated. The percent disease control was rated 7 days after the inoculation.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomator Late Blight (TLB)

Cultures of *Phytophthora infestans* were maintained on green pea-amended agar for two to three to four weeks. The spores were washed from the agar with water and dipsersed by DeVilbiss atomizer over the leaves of 3-week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Grape Downy Mildew (GDM)

*Plasmopara viticola* was maintained on leaves of live grape plants, cv. Delaware, in a controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

When tested against cucumber powdery mildew at a dose of 300 grams per hectare, compounds 1.01 and 1.34 exhibited 99% or better control.

When tested against *septoria nodorum* at 300 grams per hectare compounds 1.01, 1.34 and 2.10 exhibited 85% or better control.

When tested against wheat leaf rust at 300 grams per hectare compounds 1.01, 1.34 and 2.01 exhibited 99% or better control.

When tested against wheat powdery mildew at 300 grams per hectare compound 1.01 exhibited 95% or better control.

When tested against grape downy mildew at 300 grams/hectare compounds 1.01 and 1.34 exhibited 75% or better control.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per humdred kilograms of seed. As a soil fungicide the chemical can be incorporated in the soil or applied to the surface usually at a rate of from about 0.02 to about 20, preferably from about 0.05 to about 10, and more preferaby from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomator early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat *septoria nodorum,* rice sheath blight and rice blast.

The compounds of th present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Kekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic enviornment. If desired, adjuvants such as surfactants, stabilizers, antifoam agents and anti-drift agents may also be combined.

Examples of compositions and formulations according to the invention are aqueous solution and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the prepration of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide, such as that sold under the trademark Hi-SilR, and 5 parts of sodium lignosulfonate. In another preparation of kaolin type (Barden) clay is used in place of the Hi-Sil in the above wettable powder, and in another such preparation 25% of the Hi-Sil is replaced with a synthetic sodium silicoaluminate sold under the trademark Zeolex®3.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low volume sprays, airblast spray, aerial sprays, and dusts.

The present invention also contemplates methods of killing, combatting or controlling pests which comprises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. Compound having the structure

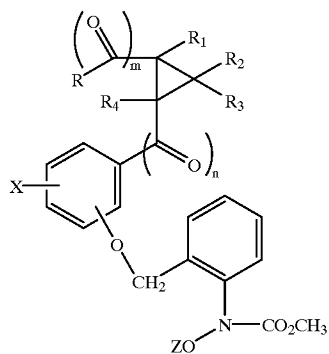

wherein m and n integers selected from 0 and 1, provided that m+n is 0 or 1;

X is selcted from the group consisting of hydrogen, halo, $(C_1–C_4)$alkyl, and $(C_1–C_4)$alkoxy;

Z is selected from the group consisting of $(C_1–C_{12})$alkyl and halo$(C_1–C_{12})$alkyl;

R is independently selected from hydrong, $(C_1–C_{12})$alkyl, $(C_1–C_{12})$alkoxy, halo$(C_1–C_{12})$alkynyl, halo$(C_2–C_{12})$alkynyl, $(C_1–C_{12})$alkoxy$(C_1–C_{12})$alkyl, $(C_1–C_{12})$alkoxy$(C_2–C_{12})$alkenyl, $C_1–C_{12})$alkoxy$(C_2–C_{12})$alkynyl, $(C_2–C_{12})$alkenyl$(C_1–C_{12})$alkoxy, $(C_2–C_{12})$alkynyl$(C_1–C_{12})$alkoxy, $(C_2–C_{12})$alkynyl$(C_2–C_{12})$alkenyl, $(C_2–C_{12})$alkenyl$(C_2–C_{12})$alkynyl, $(C_3–C_7)$cycloalkyl, halo$(C_3–C_7)$cycloalkyl, $(C_3–C_7)$cycloalkyl$(C_1–C_{12})$alkyl, $(C_3–C_7)$cycloalkyl$(C_2–C_{12})$alkenyl, $(C_3–C_7)$cycloalkyl$(C_2–C_{12})$alkynyl, $(C_1–C_{12})$alkyl$(C_3–C_7)$cycloalkyl, $(C_1–C_{12})$alkoxy$(C_3–C_7)$cycloalkyl, $(C_2–C_{12})$alkenyl$(C_3–C_7)$cycloalkyl, $(C_2–C_{12})$alkynyl$(C_3–C_7)$cycloalkyl, halo$(C_1–C_{12})$alkyl$(C_3–C_7)$cycloalkyl, halo$(C_1–C_{12})$alkoxy$(C_3–C_7)$cycloalkyl, halo$(C_2–C_{12})$alkenyl$(C_3–C_7)$cycloalkyl, halo$(C_2–C_{12})$alkynyl$(C_3–C_7)$cycloalkyl, halo$(C_3–C_7)$cycloalkyl$(C_3–C_7)$cycloalkyl, $(C_1–C_{12})$alkoxy$(C_1–C_{12})$alkyl$(C_3–C_7)$cycloalkyl, $(C_1–C_{12})$alkoxy$(C_2–C_{12})$alkenyl$(C_3–C_7)$cycloalkyl, $(C_2–C_{12})$alkenyl$(C_1–C_{12})$alkoxy$(C_3–C_7)$cycloalkyl, $(C_1–C_{12})$alkoxy$(C_2–C_{12})$alkynyl$(C_3–C_7)$cycloalkyl, $(C_2–C_{12})$alkynyl$(C_1–C_{12})$alkoxy$(C_3–C_7)$cycloalkyl, $(C_2–C_{12})$alkenyl$(C_2–C_{12})$alkynyl$(C_3–C_7)$cycloalkyl, $(C_2–C_{12})$alkynyl$(C_2–C_{12})$alkenyl$(C_3–C_7)$cycloalkyl, $(C_3–C_7)$cycloalkyl$(C_3–C_7)$cycloalkyl, $(C_1–C_{12})$alkyl$(C_3–C_7)$cycloalkyl$(C_3–C_7)$cycloalkyl, $(C_2–C_{12})$alkenyl$(C_3–C_7)$cycloalkyl$(C_3–C_7)$cycloalkyl, $(C_2–C_{12})$alkynyl$(C_3–C_7)$cycloalkyl$(C_3–C_7)$cycloalkyl, $(C_1–C_{12})$alkoxy$(C_3–C_7)$cycloalkyl$(C_3–C_7)$cycloalkyl, $(C_3–C_7)$cycloalkyl$(C_1–C_{12})$alkyl$(C_3–C_7)$cycloalkyl, $(C_3–C_7)$cycloalkyl$(C_2–C_{12})$alkenyl$(C_3–C_7)$cycloalkyl, $(C_3–C_7)$cycloalkyl$(C_2–C_{12})$alkynyl$(C_3–C_7)$cycloalkyl, $(C_3–C_7)$cycloalkyl$(C_1–C_{12})$alkoxy$(C_3–C_7)$cycloalkyl, $C_3–C_7)$cycloalkyl$(C_3–C_7)$cycloalkyl$(C_3–C_7)$cycloalkyl, $(C_3–C_7)$cycloalkyl$(C_1–C_{12})$alkoxy$(C_1–C_{12})$alkyl$(C_3–C_7)$cycloalkyl, $(C_3–C_7)$cycloalkyl$(C_1–C_{12})$alkoxy$(C_2–C_{12})$alkenyl$(C_3–C_7)$cycloalkyl, $(C_3–C_7)$cycloalkyl$(C_1–C_{12})$alkoxy$(C_2–C_{12})$alkynyl$(C_3–C_7)$cycloalkyl, aryl, aralkyl, aryl$(C_1–C_{12})$alkoxy, aryl$(C_2–C_{12})$alkenyl, aryl$(C_2–C_{12})$alkynyl, aryl$(C_3–C_7)$cycloalkyl, aryloxy$(C_1–C_{12})$alkyl, aryloxy$(C_2–C_{12})$alkynyl, aryloxy$(C_2–C_{12})$alkenyl, aryl$(C_1–C_{12})$alkoxy$(C_3–C_7)$cycloalkyl, aryl$(C_2–C_{12})$alkenyl$(C_3–C_7)$cycloalkyl, aryl$(C_2–C_{12})$alkynyl$(C_3–C_7)$cycloalkyl, aryl$(C_3–C_7)$cycloalkyl$(C_3–C_7)$cycloalkyl, $(C_3–C_7)$cycloalkylaryl, aryl$(C_1–C_4)$alkyl$(C_3–C_7)$cycloalkyl.

$R_1$ and $R_4$ are independently selected from the group consisting of hydrogen, halogen $(C_1–C_{12})$alkyl, $(C_1–C_{12})$alkoxy, halo $(C_1–C_{12})$alkyl, $(C_2–C_{12})$alkenyl, $(C_2–C_{12})$alkynyl, $(C_3–C_7)$cycloalkyl, cyano, carboxy, $(C_1–C_4)$alkoxycarbonyl, and aryl;

$R_2$ and $R_3$ are independently selected from the group consisting of hydrogen, halogen, $(C_1–C_{12})$alkyl, $(C_1–C_{12})$alkoxy, halo$(C_1–C_{12})$alkyl, $(C_2–C_{12})$alkenyl, $(C_2–C_{12})$alkynyl, $(C_3–C_7)$cycloalkyl, cyano, carboxy, $(C_1–C_4)$alkoxycarbonyl, aryl and a moiety bonded at both $R_2$ and $R_3$ so as to form a $(C_3–C_7)$cycloalkyl ring; and $R_5$ and $R_6$ are independently selected from the group consisting of hydrogen, $(C_1–C_8)$alkyl, $(C_1–C_8)$alkoxy, halo$(C_1–C_8)$alkyl, $(C_2–C_8)$alkenyl, $(C_2–C_8)$alkynyl, $(C_3–C_7)$cycloalkyl, cyano, carboxy, $(C_1–C_4)$alkoxycarbonyl, and aryl wherein when m=0, R and $R_1$ are not both hydrogen.

2. The compounds of claim 1 having the structure:

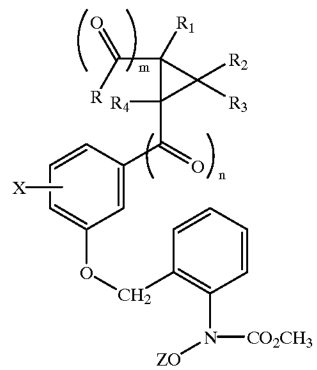

wherein:

$R_1$ and $R_4$ are hydrogen; and

R is selected from the group consisting of $(C_1–C_{12})$alkyl, halo$(C_1–C_{12})$alkyl, halosubstituted phenyl, $(C_1–C_4)$alkyl substituted phenyl, trihalosubstituted phenyl, $(C_3–C_7)$cycloalkyl, halo$(C_3–C_7)$cycloalkyl, $(C_3–C_7)$cycloalkyl$(C_1–C_{12})$alkyl, $(C_3–C_7)$cycloalkyl-$(C_2–C_{12})$alkenyl, $(C_1–C_{12})$alkyl$(C_3–C_7)$cycloalkyl and $(C_2–C_{12})$alkenyl$(C_3–C_7)$cycloalkyl.

3. The compound of claim 1 where Z is methyl.

4. The compound of claim 3 wherein n and m are zero.

5. The compound of claim 3 wherein n+m=1.

6. The compound of claim 4 wherein R is slected from the group consisting of $(C_5–C_{12})$alkyl, 2-halophenyl, 3-halophenyl, 4-halophenyl, 2-$(C_1–C_4)$alkylphenyl, 3-$(C_1–C_4)$alkylphenyl, 4-$(C_1–C_4)$alkylphenyl, cyclopropyl, cyclopropyl$(C_1–C_4)$alkyl, cyclopropyl$(C_2–C_4)$alkenyl, $(C_1–C_4)$alkylcyclopropyl, $(C_2–C_4)$alkenylcyclopropyl, 1-cyclopropylcyclopropyl and 2-cyclopropylcyclopropyl.

7. The compound of claim 5 wherein R selected from 4-chlorophenyl, 4-flourophenyl, 4-methylphenyl, cyclopropyl and 1-cyclopropyl-1-propenyl.

8. A fungicidal composition for controlling phytopathogenic fungi which comprises an agronomically acceptable carrier and the compound of claim 1 wherein the ratio of the carrier to the compound is between 99:1 and 1:4.

9. The composition of claim 8 wherein the ratio of the agronomically acceptable carrier to compound is between 10:1 and 1:3.

10. A method for controlling phytopathogenic fungi which comprises applying the compound of claim 1 to the locus where control is desired, at a rate of from 0.005 to 50 kilograms per hectare.

11. A method for controlling phytopathogenic fungi which comprises applying the compound of claim 1 to the locus where control is desired, at a rate of from 0.025 to 10 kilograms per hectare.

* * * * *